United States Patent
Davidovitch et al.

(10) Patent No.: US 9,402,998 B2
(45) Date of Patent: Aug. 2, 2016

(54) VESTIBULAR ELECTRONIC ORTHODONTIC APPLIANCE EXPEDITER AND METHOD

(71) Applicant: Rapid Orthodontics, Inc., Columbus, OH (US)

(72) Inventors: Zeev Davidovitch, Columbus, OH (US); Robert Sanford, Hampton, NJ (US); Moshe Davidovitch, Tel Aviv (IL)

(73) Assignee: RAPID ORTHODONTICS, INC., Columbus, OH (US)

( * ) Notice: Subject to any disclaimer, the term of this patent is extended or adjusted under 35 U.S.C. 154(b) by 0 days.

(21) Appl. No.: 14/821,760

(22) Filed: Aug. 9, 2015

(65) Prior Publication Data
US 2015/0343208 A1    Dec. 3, 2015

Related U.S. Application Data

(63) Continuation-in-part of application No. PCT/US2015/015409, filed on Feb. 11, 2015, which is a continuation-in-part of application No. 14/177,573, filed on Feb. 11, 2014, now abandoned.

(51) Int. Cl.
*A61C 3/00* (2006.01)
*A61N 1/18* (2006.01)
(Continued)

(52) U.S. Cl.
CPC .............. *A61N 1/18* (2013.01); *A61B 5/14539* (2013.01); *A61C 7/00* (2013.01); *A61C 7/08* (2013.01); *A61C 7/14* (2013.01); *A61C 7/20* (2013.01);
(Continued)

(58) Field of Classification Search
CPC ........... A61F 5/566; A61N 1/20; A61N 1/326
USPC ............................................................ 433/6
See application file for complete search history.

(56) References Cited

U.S. PATENT DOCUMENTS 4,153,060 A * 5/1979 Korostoff ................. A61C 7/00
                                                                  433/215
4,175,565 A   11/1979 Chiarenza et al.
(Continued)

OTHER PUBLICATIONS

Hashimoto H., Effect of micro-pulsed electricity on experimental tooth movement., Aug. 1990;49(4):352-61. PMID: 2133892 [PubMed—indexed for MEDLINE].
(Continued)

*Primary Examiner* — Nicholas Lucchesi
*Assistant Examiner* — Matthew Saunders
(74) *Attorney, Agent, or Firm* — Simon Kahn; Chanoch Kahn

(57) ABSTRACT

A vestibular electronic orthodontic appliance expediter constituted of a lingual sub-member and a buccal sub-member, the lingual sub-member arranged to fit a lingual contour of a gum of a patient, the buccal sub-member arranged to fit a buccal contour of a gum of the patient; a control circuitry; a power supply; a plurality of lingual electrodes, each associated with a particular tooth socket; and a plurality of buccal electrodes, each associated with a particular tooth socket. Either a first or a second type current is generated between lingual and buccal electrodes responsive to the control circuitry. Biochemical molecules involved in bone remodeling, augmented by the electric currents, may be applied to the expediter as a layer of gel containing those molecules on the expediter surface facing the gum tissue. Temperature control enhances the gel effects. pH measurement, as indicators of the cellular response to the combined treatment is further provided.

32 Claims, 10 Drawing Sheets

(51) Int. Cl.

| | |
|---|---|
| *A61C 19/04* | (2006.01) |
| *A61B 5/145* | (2006.01) |
| *A61C 7/00* | (2006.01) |
| *A61C 7/08* | (2006.01) |
| *A61C 7/14* | (2006.01) |
| *A61C 7/20* | (2006.01) |
| *A61N 1/05* | (2006.01) |
| *A61N 1/20* | (2006.01) |

(52) U.S. Cl.
CPC .............. *A61C 19/04* (2013.01); *A61N 1/0548* (2013.01); *A61N 1/205* (2013.01)

(56) References Cited

U.S. PATENT DOCUMENTS

| | | | | |
|---|---|---|---|---|
| 4,519,779 | A * | 5/1985 | Lieb | A61C 7/00 433/18 |
| 4,629,424 | A * | 12/1986 | Lauks | A61B 5/0002 257/417 |
| 4,854,865 | A * | 8/1989 | Beard | A61C 7/00 433/18 |
| 5,989,023 | A | 11/1999 | Summer et al. | |
| 6,089,864 | A | 7/2000 | Buckner et al. | |
| 6,598,006 | B1 | 7/2003 | Honda et al. | |
| 7,074,038 | B1 | 7/2006 | Miller | |
| 7,314,372 | B2 | 1/2008 | Belfor et al. | |
| 7,997,898 | B2 | 8/2011 | Ortiz et al. | |
| 8,083,741 | B2 | 12/2011 | Morgan et al. | |
| 8,356,993 | B1 | 1/2013 | Marston | |
| 2003/0190575 | A1 * | 10/2003 | Hilliard | A61C 7/00 433/6 |
| 2005/0048433 | A1 * | 3/2005 | Hilliard | A61C 7/00 433/24 |
| 2005/0186526 | A1 * | 8/2005 | Stewart | A61C 7/00 433/24 |
| 2006/0166157 | A1 * | 7/2006 | Rahman | A61B 5/4833 433/6 |
| 2007/0065768 | A1 * | 3/2007 | Nadav | A61C 7/006 433/6 |
| 2008/0233541 | A1 * | 9/2008 | De Vreese | A61C 19/066 433/216 |
| 2008/0248443 | A1 | 10/2008 | Chishti | |
| 2009/0117513 | A1 * | 5/2009 | Nemeh | A61C 19/063 433/32 |
| 2010/0082027 | A1 | 4/2010 | Chalmers | |
| 2011/0076636 | A1 * | 3/2011 | Wolff | A61C 19/063 433/27 |
| 2012/0094246 | A1 | 4/2012 | Pavlin | |
| 2013/0209964 | A1 * | 8/2013 | Nemeh | A61C 19/063 433/216 |
| 2013/0252193 | A1 * | 9/2013 | Bowman | A61C 7/08 433/6 |
| 2013/0280671 | A1 * | 10/2013 | Brawn | A61N 5/0603 433/24 |
| 2014/0023983 | A1 * | 1/2014 | Lowe | A61C 7/006 433/24 |
| 2014/0093832 | A1 * | 4/2014 | Nemeh | A61C 19/063 433/1 |
| 2015/0064640 | A1 * | 3/2015 | Nobrega | A61C 7/008 433/2 |

OTHER PUBLICATIONS

Kenneth, F. H. et al. "Bioelectric Perturbations in Orthodontic Tooth Movement" Journal of Dental Sciences & Research, 1(1): 41-49; published by Sri Siddhartha University, Tumkur, Karnataka—India (Feb. 2010).

Dr. Young-Guk Park; "Corticision to Accelerate Tooth Movement"; Presented by, Professor and Chair of the Department Dr. Young-Guk Park of Orthodontics, Kyung Hee University School of Dentistry, Seoul, Korea, at the PCSO Central Region Meeting, Feb. 12, 2010. Summarized by Dr. Gerald Nelson, PCSO Bulletin Editor.

Jozef Joachim Telega and Ryszard Wojnar, Piezo Electric Effects in Biological Tissue, Journal of Theoretical and applied mechanics 3, 40, 2002.

Z. Davidovitch, E. Korostoff, M. D. Finkelson, R. W. Yost, P. C. Montgomery, S. Steigman and J. L. Shanfeld, Effect of electric currents on gingival cyclic nucleotides in vivo, Journal of Periodontal Research 15: 353-362, 1980.

Anand Patil, V.P. Jayade, Jios; "Advances in Biology of Orthodontics Tooth Movement—A Review"; Journal of Indian Orthodontic Society, 2006; 39-155-164.

Brighton, Friedenberg, Mitchell and Booth; "Treatment of Nonunion with Constant Direct Current"; Clinical Orthopaedics and Related Research, No. 124, pp. 106-123, May 1977, published by Springer Healthcare Ltd. online at www.clinorthop.org.

Kim, Dong-Hwan et al. abstract of "The effects of electrical current from a micro-electrical device on tooth movement" 38(5): 337-346; published by Korean Association of Orthodontists (Oct. 2008).

Davidovitch, Zeev et al. summary of "Biochemical mediators of the effects of mechanical forces and electric currents on mineralized tissues" Calcified Tissue International; 36(1 Supplement): S86-S97; published by Springer-Verlag (Mar. 1984).

Davidovitch, Zeev et al. "Electric currents, bone remodeling, and orthodontic tooth movement: I. The effect of electric currents on periodontal cyclic nucleotides" American Journal of Orthodontics, 77(1): 14-32; published by American Association of Orthodontists (Jan. 1980).

Regence "Medical Policy Manual", Electrical Bone Growth Stimulators, Published online at blue.regence.com by Regence Oregon and Utah, Jan. 1996.

International Search Report for PCT/US2015/015409 issued May 13, 2015 by the European Patent Office.

Written Opinion of the International Searching Authority for PCT/US2015/015409 issued May 13, 2015 by the European Patent Office.

* cited by examiner

VESTIBULAR ELECTRONIC ORTHODONTIC APPLIANCE EXPEDITER AND METHOD

CROSS REFERENCE TO RELATED APPLICATIONS

This application is a continuation in part of PCT application S/N PCT/US2015/015409 filed Feb. 11, 2015 of the same title, which claims priority from U.S. application Ser. No. 14/177,573, filed Feb. 11, 2014 and entitled "Method to enhance orthodontic tooth movement", the entire contents of both of which are incorporated herein by reference.

TECHNICAL FIELD

The invention relates generally to the field of orthodontic tooth movement and in particularly to a vestibular electronic orthodontic appliance expediter and method.

BACKGROUND

Over the past 25 centuries, orthodontists have been engaged in the process of repositioning teeth from faulty arrangements, or "malocclusions," into healthier and more esthetic arrangements. In order to move teeth, three elements are generally required: 1) force, 2) time and 3) space. The mouth responds to a sustained force placed on a tooth by rearranging, or "remodeling," the alveolar bone around the root of the tooth. Particularly, osteoclasts break down bone in the area where the tooth is being moved to in order to create space for the tooth. As a result, the tooth is able to move in the direction of the force applied thereto. Additionally, osteoblasts form new bone tissue in the area where the tooth is being moved from.

In further detail, FIGS. 1A-1B illustrate a "remodeling" of the alveolar bone. As illustrated in FIG. 1A, a tooth is comprised of a crown 0 and a root 1. The crown is visible in the mouth, while the root is not, because it is encased in soft connective tissue fibrous mesh known as the periodontal ligament (PDL) 3, and PDL 3 is surrounded by alveolar bone 4. Alveolar bone 4 faces PDL 3 on one side, and is covered by gingival and mucosal tissue (gum) 5 on the other. PDL 3, alveolar bone 4 and gum 5 contain living cells which are responsible for the remodeling of all these tissues in response to orthodontic forces. This remodeling process is the mechanism that facilitates orthodontic tooth movement. The cells are attached to the matrix that surrounds them, and when they become subjected to orthodontic forces that stretch or compress them, the strain is transmitted directly to the cell nucleus and nucleolus, activating the production of multiple molecules including membrane receptors, which interact with signal molecules derived from the nervous, immune, vascular and skeletal systems.

As illustrated in FIG. 1B, physical changes result from application of an orthodontic force to crown 0 of the tooth. The mechanical forces and moments are applied to affect the desired type of tooth movement. Accordingly, a tooth may be extruded, intruded, rotated, tipped, or translated. FIG. 1B illustrates a translatory movement which results from a translational force 7 and a rotation 6 of crown 0 around a center of rotation, or fulcrum, located near the apex of root 1. In order to insure a translatory movement, a force couple is created opposite to rotational force 6. This force couple (generated by the interaction between the bracket and the arch wire for braces, and attachments and aligners for aligner devices) creates a moment that moves root 1 along with crown 0 extending the center of rotation from the apex to infinity. Translational force 7 pushes root 1 against alveolar bone 4, opposite to the point of force application, compressing a portion 9 of PDL 3. Likewise, on the side of the tooth where force 7 is being applied, a portion 8 of PDL 3 is being stretched. Root 1 is displaced within the tooth socket of alveolar bone 4, and the PDL 3 responds by widening portion 8 and compressing portion 9. The compressed portion 9 undergoes removal (resorption), while in the stretched portion 8 new layers of bone are deposited on the surface of the old alveolar bone 4. Over time, alveolar bone 4 remodels, allowing the tooth to assume a new position in the place that translational force 7 caused it to move. This remodeling is a direct result of, and consistent with, the compression/resorption and stretching/deposition activity in PDL 3 and juxtaposed alveolar bone 4. When alveolar bone 4 is pressed upon, as occurs when translational force 7 presses on a tooth and PDL 3 compresses, a short-lived electrical spike can be measured across alveolar bone's 4 matrix. This is known as a piezoelectric effect, characterized by the negative side of the potential being detected on the concave side of the flexed bone and the positive side of the potential being detected on the convex side. In addition, the mechanical stress causes movement of tissue fluids. These fluids contain electrical charges that change the cellular electric polarity, stimulating the cells to remodel their surrounding matrices. These stress-generated streaming potentials (SGP) last about 20-30 minutes. When the bone is held in a flexed state, the concave side experiences bone deposition and the convex side experiences bone resorption. As long as the bone remains flexed, this process continues over time until the previously flexed bone appears unflexed or straight.

Over the years, orthodontists have invented devices, generally referred to as "appliances", that allow clinicians to deliver sustained forces to the teeth. Braces, or "orthodontic brackets and arch wires," are the classic appliances that most, if not all orthodontists use. These forces are applied to the crowns of the teeth, then transferred to the dental roots, and from there to the tissues that surround the roots, consisting of the periodontal ligament, a thin soft tissue sleeve that embraces each root, separating it from the surrounding alveolar bone. On the outside, the alveolar bone is covered by the gum. All these tissues must remodel, in order to enable the orthodontically treated teeth to move to new positions in the jaw. Braces consist of small brackets that are glued, or "bonded," to the crowns of teeth, and a wire is then inserted into slots in the brackets and held in place with a ligature or clip. The brackets do not generate forces themselves, but rather transfer forces to the teeth from the deflected wire, when it is inserted into the slot in the bracket and held in place by the ligature. The wire has a "memory," i.e., a characteristic by which the wire tends to return to its original shape, and in doing so, exerts a force on the bracket that is in turn transmitted to the tooth. Through the application of various types, shapes and sizes of wires, the teeth eventually align themselves into the desired position in the dental arch. The technical term used among orthodontists to describe braces is "comprehensive fixed appliance". The tooth movement is clarified by Wolff's Law, which states, in effect, that bone under mechanical stress is remodeled to accommodate and reduce the stress.

Bone cells are responsive to various physical and chemical agents, amongst them: mechanical force and electricity. When direct current, in the order of 20 µA, is applied to bone, deposition of new bone matrix occurs near the cathode, while destruction of old bone is found near the anode. This feature, as well as the ability of bone cells to respond simultaneously to force and electricity, create a favorable environment for acceleration of the rate of bone remodeling and, consequently, the speed of tooth movement. Due to a synergistic relationship between applied force and applied electricity, when both force and electricity are applied simultaneously less of each are necessary to achieve an optimally enhanced osteogenic response from the bone.

Typical orthodontic appliances must be worn by the patient for extended periods of time, often several years or more, in order to achieve the desired results. The classic orthodontic treatment that requires the continuous application of forces to attain the planned tooth movement is expensive, as it requires frequent modifications of the magnitude and direction of forces applied to different teeth, to achieve the necessary progress, requiring frequent adjustments by the treating orthodontist. Moreover, wearing the mechanical fixtures known as "braces" creates a considerable discomfort for the patient, and at the same time this condition will cause an aesthetic concern to the patient as the metallic fixtures (Braces) are visible to other people. In addition, the braces promote the accumulation of bacteria and viruses, harmful to the teeth and their surrounding tissues.

In order to overcome some of the above disadvantages, orthodontic appliances have been developed that can be inserted and removed by the patient, and worn part-time. A myriad of removable appliances have been developed over the years, but the vast majority are not "comprehensive" in nature, i.e. the removable appliances address specific movements or malocclusions, and are only used for a certain limited period of time. Treatment with removable appliances is often used in conjunction with braces or other appliances. The wish to shorten the duration of orthodontic treatment is universal, for obvious reasons. It has led to the development of surgical procedures, which are invasive in nature, and aimed at causing wide-spread inflammation and wound healing, leading to rapid tooth movement.

U.S. Pat. No. 4,153,060, issued on May 8, 1979 to Korostoff et al., the entire contents of which are incorporated herein by reference, teaches a method and apparatus for electrically stimulating alveolar bone remodeling and tooth movement in the mouths of humans. A positive electrode is placed on the gum surface adjacent the bone structure which is to be resorbed. A negative electrode is placed on the gum surface adjacent the bone tissue which is to be accreted or built up. A current source is connected, such that a small current flows between the electrodes, which have the effect of stimulating bone growth in a specific direction. In a particular arrangement, the electrodes are placed on the gum surface adjacent a tooth, the positive electrode on the side towards which the tooth should move, and the negative on the side from which the tooth will move. Application of a small current to the electrodes will enhance the repositioning of the tooth in conjunction with normal orthodontic practices. However, Korostoff fails to provide a comprehensive and effective system for reducing orthodontic treatment time. Additionally, the electrodes of Korostoff tend to cause excessive irritation of the gums. Although several decades have passed, the method of Korostoff has not achieved wide use by orthodontists.

U.S. Pat. No. 4,854,865, issued Aug. 8, 1989 to Beard et al., teaches an improved method of orthodontic electro-osteogenesis using a biocompatible anode in contact with an electrolytic gel between the anode and epithelial gingiva at an area of osteoclastic or osteoblastic activity, and a biocompatible cathode in contact with a different type of electrolytic gel between the cathode and epithelial gingiva at an area of osteoclastic or osteoblastic activity. Current is then applied across the anode and cathode to stimulate osteogenesis. This method stimulates osteogenesis, which is an important element in tooth movement, but is unable to demonstrate how to achieve desirable results, or to enable to complete orthodontic treatment in a shorter amount of time.

U.S. patent application publication US 2014/0023983, published Jan. 23, 2014 to Lowe et al., the entire contents of which is incorporated herein by reference, is addressed to an electro-orthodontic appliance which helps accelerate orthodontic tooth movement through the application of a controlled electric current to gum and teeth, thus stimulating osteogenesis. Lowe does not provide a comprehensive solution for enhancing orthodontic tooth movement in a plurality of treatment situations, including a combination of bodily and tipping movements of a plurality of teeth. Additionally, the system of Lowe evokes root resorption due to stimulation of cells residing on the surface of the dental root, which is undesirable.

U.S. patent application publication US 2009/0117513, published May 7, 2009 to Nemeh et al., the entire contents of which is incorporated herein by reference, is addressed to a method and apparatus for concurrent treatment of multiple oral diseases and defects while promoting general oral hygiene utilizing direct current electricity applied to the gingival tissues of the mouth. Nemeh does not provide a system or method of utilizing this electricity for improvement of orthodontic treatment. It is therefore an object of the present disclosure to overcome at least part of the disadvantages of the prior art.

SUMMARY OF THE INVENTION

Accordingly, it is a principal object of the present invention to overcome disadvantages of prior art methods and arrangements of orthodontic tooth movement. In one embodiment, a vestibular electronic orthodontic appliance expediter is enabled, comprising: a lingual sub-member and a buccal sub-member, the lingual sub-member arranged to fit a lingual contour of a gum of a patient over a lingual side of an alveolar bone of the patient, the buccal sub-member arranged to fit a buccal contour of a gum of the patient over a buccal side of the alveolar bone; a control circuitry; a power supply disposed within the vestibular electronic brace; a plurality of lingual electrodes, each of the plurality of lingual electrodes adapted to be juxtaposed with the lingual side of the alveolar bone of the patient and associated with a particular one of a plurality of tooth sockets within the alveolar bone; and a plurality of buccal electrodes, each of the plurality of buccal electrodes adapted to be juxtaposed with the buccal side of the alveolar bone of the patient and associated with a particular one of the plurality of tooth sockets within the alveolar bone, wherein, responsive to the control circuitry and the power supply, a first type current is generated between each of the plurality of lingual electrodes and a particular one of the plurality of buccal electrodes, or a second type current is generated between each of adjacent ones of the plurality of lingual electrodes and between adjacent ones of the plurality of buccal electrodes, and wherein each of the generated first type currents, or each of the generated second type currents, is controlled separately responsive to the control circuitry.

In one further embodiment, the lingual sub-member and a buccal sub-member are formed into a single contiguous member. In yet further embodiment the control circuitry and the power supply are each disposed within the single contiguous member.

In one further embodiment the direction of each of the generated first type currents, or the direction of each of the generated second type currents, is arranged to expedite bone resorption or deposition caused responsive to an orthodontic force applied to a tooth disposed within the respective tooth socket by an orthodontic appliance. In another further embodiment, responsive to the control circuitry and the power supply, a plurality of the first type currents and a plurality of the second type currents are generated.

In one further embodiment, the vestibular electronic orthodontic appliance expediter further comprises a plurality of electrical paths isolated from each other, the control circuitry in electrical communication with each of the plurality of lingual electrodes, or with each of the plurality of buccal electrodes, via a respective one of the plurality of electrical paths. In another further embodiment, the control circuitry comprises a user input module arranged to receive a current polarity selection user input, wherein responsive to a particular current polarity selection user input received at the user input module, the direction of the generated first type current between a first of the plurality of lingual electrodes and a first of the plurality of buccal electrodes opposes the direction of the generated first type current between a second of the plurality of lingual electrodes and a second of the plurality of buccal electrodes, or the direction of the generated second type current between a pair of adjacent ones of the plurality of lingual electrodes opposes the direction of the generated second type current between a pair of adjacent ones of the plurality of buccal electrodes, associated with the adjacent ones of the plurality of lingual electrodes.

In one further embodiment, the control circuitry comprises a user input module arranged to receive an electrode selection user input, wherein responsive to a particular electrode selection user input received at the user input module, a first type current is generated between a first of the plurality of lingual electrodes and a first of the plurality of buccal electrodes, and a first type current is not generated between a second of the plurality of lingual electrodes and a second of the plurality of buccal electrodes, or a second type current is generated between a first pair of adjacent ones of the plurality of lingual electrodes and between a first pair of adjacent ones of the plurality of buccal electrodes, and a second type current is not generated between a second pair of adjacent ones of the plurality of lingual electrodes and between a second pair of adjacent ones of the plurality of buccal electrodes.

In one further embodiment, a third of the plurality of lingual electrodes is adapted to be juxtaposed with a first side of a particular tooth socket, and a fourth of the plurality of lingual electrodes is adapted to be juxtaposed with a second side of the particular tooth socket, the second side of the tooth socket opposing the first side of the tooth socket, wherein a third of the plurality of buccal electrodes, associated with the third of the plurality of lingual electrodes, is adapted to be juxtaposed with the first side of the particular tooth socket, and a fourth of the plurality of buccal electrodes, associated with the fourth of the plurality of lingual electrodes, is adapted to be juxtaposed with the second side of the particular tooth socket, and wherein the direction of the first type current generated between the third of the plurality of lingual electrodes and the third of the plurality of buccal electrodes opposes the direction of the first type current generated between the fourth of the plurality of lingual electrodes and the fourth of the plurality of buccal electrodes, or the direction of the second type current generated between the third and fourth of the lingual electrodes opposes the direction of the second type current generated between the third and fourth buccal electrodes. In one yet further embodiment, the vestibular electronic orthodontic appliance expediter further comprises a second orthodontic appliance arranged to provide a rotation force to a tooth having a root within the particular tooth socket, the rotational orthodontic force arranged to generate rotational motion of the tooth, the generated rotation motion defining: a first motion vector in a first direction at a portion of a first side of the tooth; and a second motion vector, in a second direction opposing the first direction, at a portion of a second side of the tooth, the second side of the tooth opposing the first side of the tooth; wherein a first axis extending between the third of the plurality of lingual electrodes and the third of the plurality of buccal electrodes is parallel and aligned with the first motion vector, or a second axis extending between the third and fourth of the plurality of lingual electrodes is parallel and aligned with the first motion vector, wherein a third axis extending between the fourth of the plurality of lingual electrodes and the fourth of the plurality of buccal electrodes is parallel and aligned with the second motion vector, or a fourth axis extending between the third and fourth of the plurality of buccal electrodes is parallel and aligned with the second motion vector, and wherein the direction of the first type current generated between the third of the plurality of lingual electrodes and the third of the plurality of buccal electrodes and the direction of the first type current generated between the fourth of the plurality of lingual electrodes and the fourth of the plurality of buccal electrodes are arranged to expedite bone resorption and deposition caused responsive to the provided rotational orthodontic force, or the direction of the second type current generated between the third and fourth lingual electrodes and the direction of the second type current generated between the third and fourth buccal electrodes are arranged to expedite bone resorption and deposition caused responsive to the provided rotation orthodontic force.

In one further embodiment for each of the generated first or second type currents, the control circuitry is arranged such that the generated first or second type current is alternately provided for a predetermined active duration and not provided for a predetermined quiescent duration, the predetermined active duration being 3-5 hours. In another further embodiment, the vestibular electronic orthodontic appliance expediter further comprises a plurality of adjustable pressure elements, each of the adjustable pressure elements arranged to apply an adjustable amount of pressure to a respective one of the plurality of lingual electrodes and the plurality of buccal electrodes. Optionally, each of the adjustable pressure elements is arranged to expand responsive to air being injected therewithin, the adjustable amount of pressure applied responsive to the injected air; and/or each of the adjustable pressure elements is arranged to expand responsive to a pressure member being inserted therewithin, the adjustable amount of pressure applied responsive to the inserted pressure member.

In one further embodiment the vestibular electronic orthodontic appliance expediter further comprises: a temperature sensor arranged to sense the temperature of the gums of the alveolar bone; and a heating element arranged to heat the gums of the alveolar bone, responsive to the sensed temperature. Optionally, the heating element is an IR LED which further provides light to the gums of the alveolar bone to at least temporarily increase blood circulation. In another further embodiment the vestibular electronic orthodontic appliance expediter further comprises a pH sensor arranged to sense the pH level of the gums of the alveolar bone, wherein the magnitude of the first type currents or the second type currents are adjusted responsive to the sense pH level.

In one further embodiment, at least a portion of an oral mucosa facing surface of one of the lingual sub-member and the buccal sub-member are coated with a gel comprising an active section of molecules from one of: parathyroid hormone (PTH); vitamin D3; prostaglandin E2 (PGE2); and interleukin 1 beta (IL-1β).

Independently, a method of expediting orthodontic tooth adjustment is enabled, the method comprising: providing a lingual sub-member and a buccal sub-member, the lingual sub-member arranged to fit a contour of a gum of a patient over a lingual side of an alveolar bone of the patient, the buccal sub-member arranged to fit the contour of the gum over the buccal side of the alveolar bone of the patient; providing a plurality of lingual electrodes, each of the plurality of lingual electrodes adapted to be juxtaposed with the lingual side of the alveolar bone of the patient and associated with a particular one of a plurality of tooth sockets within the alveolar bone; providing a plurality of buccal electrodes, each of the plurality of buccal electrodes adapted to be juxtaposed with a buccal side of the alveolar bone of the patient and associated with a particular one of the plurality of tooth sockets within the alveolar bone; generating a first type current between each of a plurality of lingual electrodes and a particular one of a plurality of buccal electrodes, or a second type current between each of adjacent ones of the plurality of lingual electrodes and between adjacent ones of a plurality of buccal electrodes, each of the plurality of lingual electrodes adapted to be juxtaposed with a lingual side of an alveolar bone and associated with a particular one of a plurality of tooth sockets within the alveolar bone and each of the plurality of buccal electrodes adapted to be juxtaposed with a buccal side of the alveolar bone and associated with a particular one of the plurality of tooth sockets within the alveolar bone, wherein each of the generated first type currents, or each of the generated second type currents, is controlled separately responsive to a control circuitry.

In one further embodiment the direction of each of the generated first type currents, or the direction of each of the generated second type currents, is arranged to expedite bone resorption or deposition caused responsive to an orthodontic force applied to a tooth disposed within the respective tooth socket. In another further embodiment a plurality of the first type currents and a plurality of the second type currents are generated.

In one further embodiment the separate controlling by the control circuitry is via a plurality of electrical paths isolated from each other. In another further embodiment the method further comprises: receiving a particular current polarity selection user input, wherein responsive to the received particular current polarity selection user, the direction of the generated first type current between a first of the plurality of lingual electrodes and a first of the plurality of buccal electrodes opposes the direction of the generated first type current between a second of the plurality of lingual electrodes and a second of the plurality of buccal electrodes, or the direction of the generated second type current between adjacent ones of the plurality of lingual electrodes opposes the direction of the generated second type current between adjacent ones of the plurality of buccal electrodes, associated with the adjacent ones of the plurality of lingual electrodes.

In one further embodiment the method further comprises receiving a particular electrode selection user input, wherein responsive to the received particular electrode selection user input, a first type current is generated between a first of the plurality of lingual electrodes and a first of the plurality of buccal electrodes, and a first type current is not generated between a second of the plurality of lingual electrodes and a second of the plurality of buccal electrodes, or a second type current is generated between a first pair of adjacent ones of the plurality of lingual electrodes and between a first pair of adjacent ones of the plurality of buccal electrodes, and a second type current is not generated between a second pair of adjacent ones of the plurality of lingual electrodes and between a second pair of adjacent ones of the plurality of buccal electrodes. In another further embodiment a first of the generated first type currents is associated with a first side of a particular one of the plurality of tooth sockets and a second of the generated first type currents is associated with a second side of the particular one of the plurality of tooth sockets, opposing the first side of the particular one of the plurality of tooth sockets, the direction of the second of the generated first type currents opposing the direction of the first of the generated first type currents, or a first of the generated second type currents is associated with a third side of the particular one of the plurality of tooth sockets and a second of the generated second type currents is associated with a fourth side of the particular one of the plurality of tooth sockets, opposing the third side of the particular one of the plurality of tooth sockets, the direction of the second of the generated second type currents opposing the direction of the first of the generated second type currents. Optionally, the method further comprises providing a rotational orthodontic force to a tooth having a root within the particular tooth socket, the rotational orthodontic force arranged to generate rotational motion of the tooth, the generated rotation motion defining: a first motion vector in a first direction at a portion of a first side of the tooth, the first of the generated first type currents, or the first of the generated second type currents, parallel and aligned with the first motion vector; and a second motion vector, in a second direction opposing the first direction, at a portion of a second side of the tooth, the second side of the tooth opposing the first side of the tooth, the second of the generated first type currents, or the second of the generated second type currents, parallel and aligned with the second motion vector.

In one further embodiment each of the generated first or second type currents is alternately provided for a predetermined active duration and not provided for a predetermined quiescent duration, the predetermined active duration being 3-5 hours. In another further embodiment the method further comprises applying an adjustable amount of pressure to a set of the plurality of lingual electrodes and the plurality of buccal electrodes. Optionally, the method further comprises injecting air within each of a plurality of adjustable pressure elements, the adjustable amount of pressure applied responsive to the injected air; and/or inserting a pressure member within each of a plurality of adjustable pressure elements, the adjustable amount of pressure applied responsive to the inserted pressure members.

In one further embodiment the method further comprises sensing the temperature of the gums of the alveolar bone; and adjusting the temperature of the gums responsive to the sensed temperature. Optionally, the heating element is an IR LED which further provides light to the gums of the alveolar bone to at least temporarily increase blood circulation. In another further embodiment the method further comprises sensing the pH level of the gums of the alveolar bone; and adjusting the magnitude of the generated first type current or second type current responsive to the sensed pH level.

In one further embodiment the method further comprises: coating at least a portion of an oral mucosa facing surface of one of the provided lingual sub-member and the provided buccal sub-member with a gel comprising an active section of molecules from one of: parathyroid hormone (PTH), vitamin D3; prostaglandin E2 (PGE2); and interleukin 1 beta (IL-1β).

Additional features and advantages of the invention will become apparent from the following drawings and description.

BRIEF DESCRIPTION OF THE DRAWINGS

For a better understanding of the invention and to show how the same may be carried into effect, reference will now be made, purely by way of example, to the accompanying drawings in which like numerals designate corresponding elements or sections throughout.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings.

DETAILED DESCRIPTION OF THE PREFERRED EMBODIMENTS

Figure 1A:
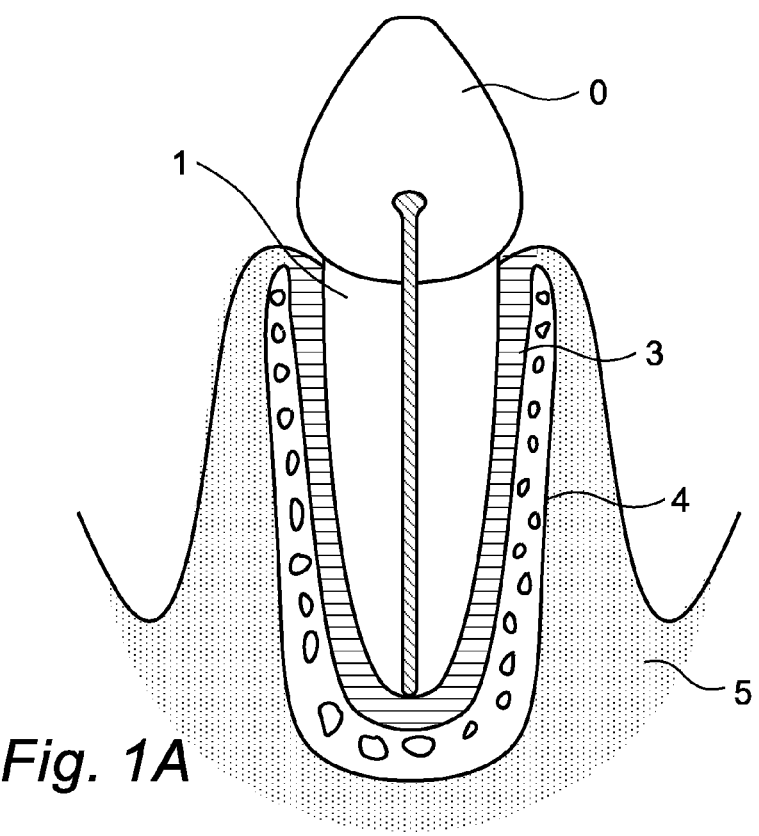
FIGS. 1A-1B illustrate bone "remodeling" of an alveolar bone responsive to orthodontic appliance pressure applied to a tooth.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

Advantageously, the subject device is non-invasive, utilizing increased understanding of the biological nature of orthodontics, on the cellular and molecular levels.

As indicated above, when the cells become subjected to orthodontic forces that stretch or compress them, the strain is transmitted directly to the cell nucleus and nucleolus, activating the production of multiple molecules including membrane receptors, which interact with signal molecules derived from the nervous, immune, vascular and skeletal systems. This ability to interact simultaneously with a number of stimulating factors creates a situation where the orthodontist can affect the extent of cellular functions by adding to the orthodontic force single or multiple stimulatory agents, like heat, light, and electricity, or a variety of inflammatory mediators, thereby increasing the velocity of tissue remodeling and tooth movement, As indicated above, there is a synergistic relationship between applied force and applied electricity, when both force and electricity are applied simultaneously less of each are necessary to achieve an optimally enhanced osteogenic response from the bone. The same principle pertains to the application of inflammatory mediators to tissues subjected to orthodontic forces: only minimal amounts of the stimulatory agents are required for producing a synergistic effect.

Figure 2A:
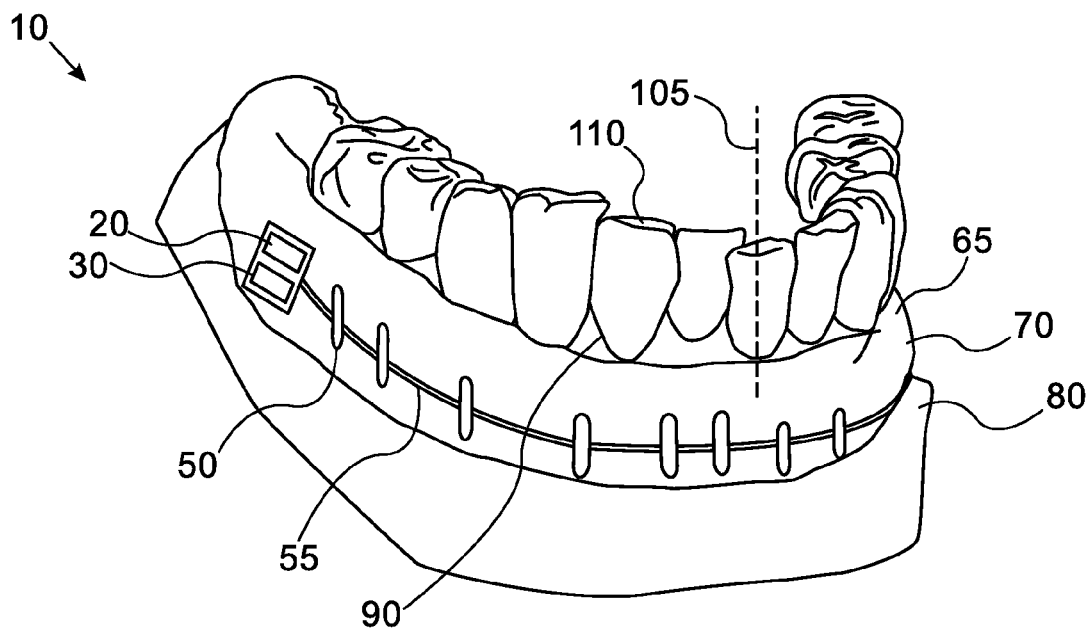
FIGS. 2A-2D illustrate various high level views of a first embodiment of an vestibular electronic orthodontic appliance expediter, according to certain embodiments.
Figure 2B:
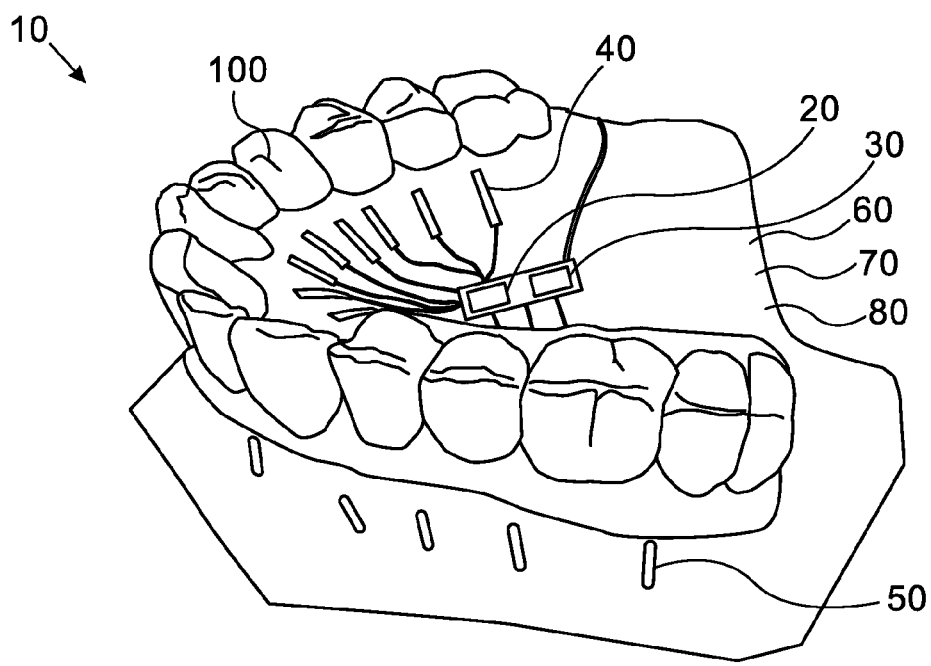

FIGS. 2A-2B illustrate various a high level perspective views of a vestibular electronic orthodontic appliance expediter 10, according to certain embodiments. Vestibular electronic orthodontic appliance expediter 10 comprises: a control circuitry 20; a power supply 30; a plurality of lingual electrodes 40; and a plurality of buccal electrodes 50. In one embodiment, power supply 30 is rechargeable. In one further embodiment, power supply 30 comprises a Nickel-Cadmium rechargeable battery. In another further embodiment, power supply 30 comprises a Lithium rechargeable battery.

Each lingual electrode 40 is adapted to be juxtaposed with a lingual side 60 of an alveolar bone 70. In one embodiment, as will be described below, plurality of lingual electrodes 40 are disposed on a lingual member (not shown) arranged to fit the contour of the gum 80 over lingual side 60 of alveolar bone 70. Each lingual electrode 40 is associated with a particular one of a plurality of tooth sockets 90 within alveolar bone 70. Particularly, in one illustrated embodiment each lingual electrode 40 is positioned between two adjacent tooth sockets 90, i.e. between two adjacent teeth 100. In another embodiment (not shown), a pair of lingual electrodes 40 are positioned between each pair of adjacent tooth sockets 90, a first of the pair of lingual electrodes 40 in proximity to a first of the pair of adjacent tooth sockets 90 and a second of the pair of lingual electrodes 40 in proximity to a second of the pair of adjacent tooth sockets 90.

Each buccal electrode 50 is adapted to be juxtaposed with a buccal side 65 of alveolar bone 70. In one embodiment, as will be described below, plurality of buccal electrodes 50 are disposed on a buccal member (not shown) arranged to fit the contour of the gum 80 over buccal side 65 of alveolar bone 70. Each buccal electrode 50 is associated with a particular one of tooth sockets 90. Particularly, in one illustrated embodiment each buccal electrode 50 is positioned between two adjacent tooth sockets 90, i.e. between two adjacent teeth 100. In another embodiment (not shown), a pair of buccal electrodes 50 are positioned between each pair of adjacent tooth sockets 90, a first of the pair of buccal electrodes 50 in proximity to a first of the pair of adjacent tooth sockets 90 and a second of the pair of buccal electrodes 50 in proximity to a second of the pair of adjacent tooth sockets 90.

In one embodiment, each lingual electrode 40 and buccal electrode 50 is generally longitudinally shaped and extends along an axis generally parallel with a longitudinal axis 105 of each tooth 100. In another embodiment, each lingual electrode 40 and buccal electrode 50 extends from about 1 millimeter apical to the gingival margin to the mucogingival junction of gums 80, further optionally extending 1-2 millimeters over the mucosal tissue. In one further embodiment, each lingual electrode 40 and buccal electrode 50 is 5-6 millimeters in length.

Power source 30 and control circuitry 20 are coupled to each of plurality of lingual electrodes 40 and plurality of buccal electrodes 50 via a respective one of a plurality of electrical paths 55. Preferably, electrical paths 35 are isolated from each other such that control circuitry 20 is arranged to separately control each lingual electrode 40 and buccal electrode 50, as will be described below. In one embodiment, electrical paths 35 are bundled together within a single isolation material. In one embodiment, each lingual electrode 40 and buccal electrode 50 is arranged to be alternately coupled to a first and a second voltage terminal of power source 30. In such an embodiment, control circuitry 20 is arranged to select for each lingual electrode 40 and buccal electrode 50 to which voltage terminal of power source 30 to be coupled to, as will be described below. In another embodiment, lingual electrodes 40 are each coupled to a first voltage terminal of power source 30 and buccal electrodes 50 are each arranged to be alternately coupled to a second and a third voltage terminal of power source 30, the potential at the second voltage terminal greater than the potential at the first voltage terminal and the potential at the third voltage terminal less than the potential at the first voltage terminal. In such an embodiment, control circuitry 20 is arranged to select for each buccal electrode 50 to which voltage terminal of power source 30 to be coupled to, as will be described below.

In another alternate embodiment, buccal electrodes 50 are each coupled to a first voltage terminal of power source 30 and lingual electrodes 40 are each arranged to be alternately coupled to a second and a third voltage terminal of power source 30, the potential at the second voltage terminal greater than the potential at the first voltage terminal and the potential at the third voltage terminal less than the potential at the first voltage terminal. In such an embodiment, control circuitry 20 is arranged to select for each lingual electrode 40 to which voltage terminal of power source 30 to be coupled to, as will be described below.

Electrical paths 35 connecting control circuitry 20 and power source 30 to buccal electrodes 50 are not shown in FIG. 2B for simplicity.

Figure 1B:
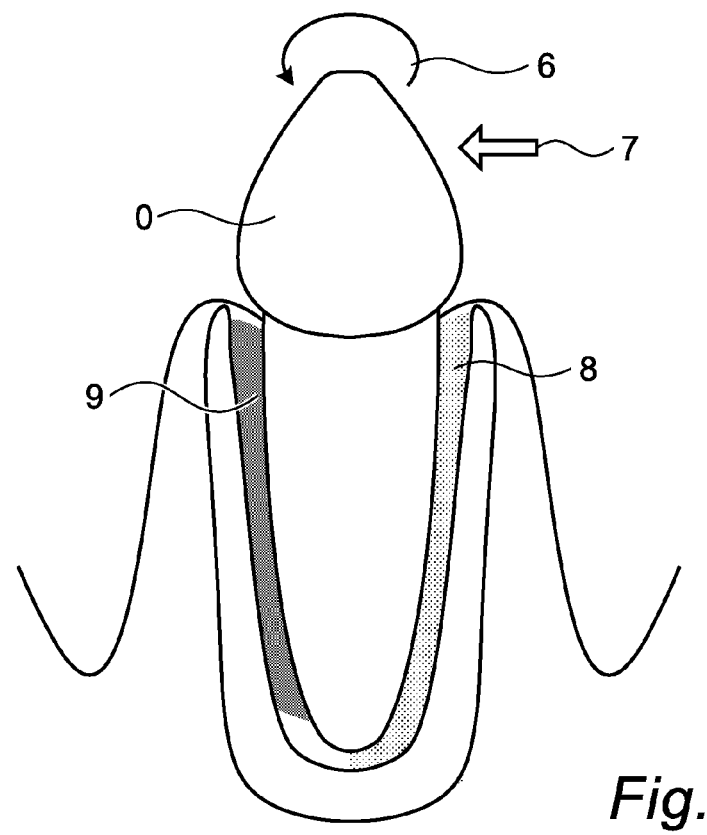
Figure 2C:
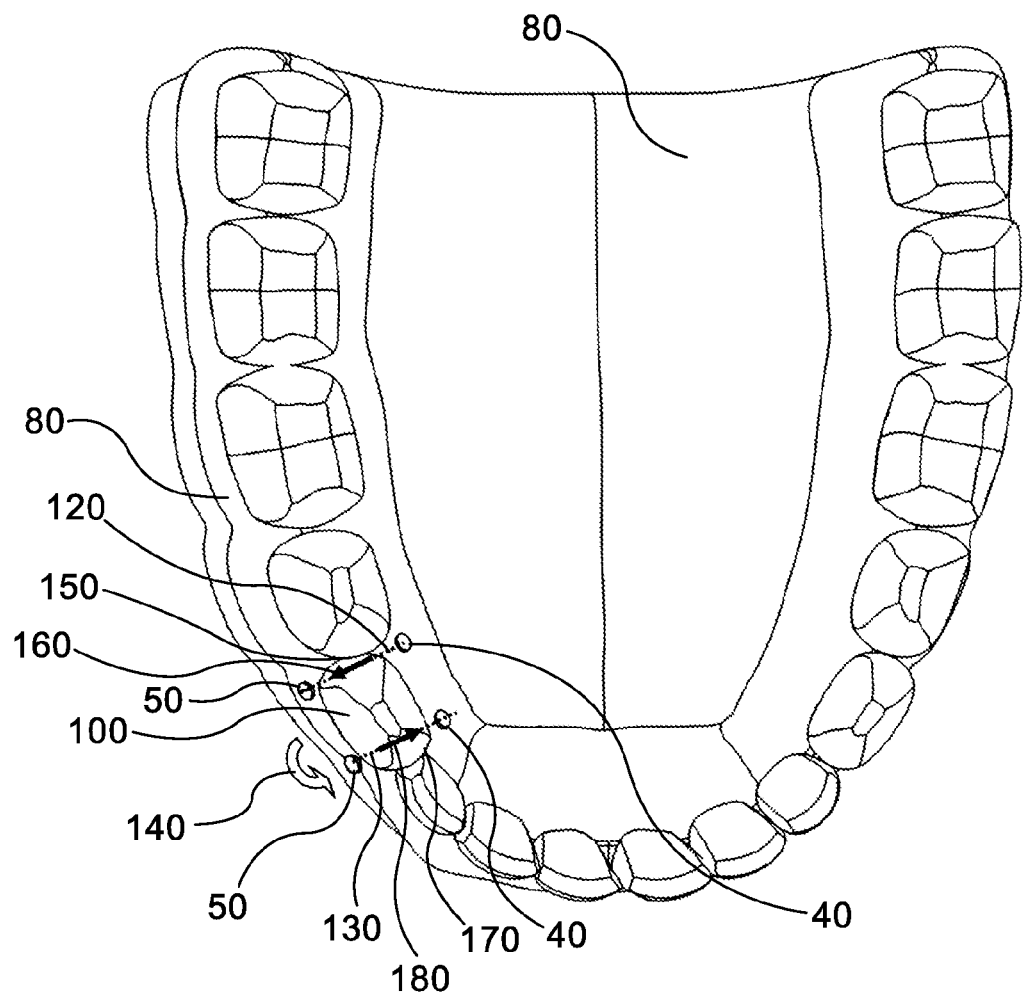

In operation, and as will be described further in relation to FIG. 7, an orthodontic appliance such as braces, is connected to teeth 100 and applies pressure to straighten teeth 100. Each tooth 100 which is not in a correct position, i.e. either crooked or out of line with the remainder of teeth 100, has pressure applied thereto by the orthodontic appliance. The pressure applied by the orthodontic appliance moves each of the respective teeth 100 into the appropriate position, as described above in relation to FIGS. 1A-1B. Control circuitry 20 is arranged to control power source 30 to generate a current between each lingual electrode 40 and an associated lingual electrode 40 or buccal electrode 50. Particularly, each tooth 100 has associated therewith two lingual electrodes 40 and two buccal electrodes 50, as illustrated in FIG. 2C, an axis 120 passing through a first lingual electrode 40 and a first buccal electrode 50 at a first side of tooth 100 and an axis 130 passing through a second lingual electrode 40 and a second buccal electrode 50 at a second side of tooth 100. Only a single pair of lingual electrodes 40 and buccal electrodes 50 are illustrated in FIG. 2C for simplicity, however this is not meant to be limiting in any way. Additionally, the movement of tooth 100 in FIG. 1C is illustrated as a rotational movement, however this is not meant to be limiting in any way.

In the event that tooth 100 needs to be moved lingually, i.e. towards the tongue, a first and a second orthogonal current are generated. The term 'orthogonal current' as used herein means that the current flows in a direction generally orthogonal to the gum line of alveolar bone 70. Particularly, the first orthogonal current is arranged to flow from the first lingual electrode 40 to the first buccal electrode 50, along axis 120, and the second orthogonal current is arranged to flow from the second lingual electrode 40 to the second buccal electrode 50, along axis 130. Responsive to the forces applied by the orthodontic appliance, bone resorption begins on the lingual side of the respective tooth 100 and bone deposition begins on the buccal side of tooth 100. The first and second generated orthogonal currents aid and expedite bone resorption in the vicinity of each of first lingual electrode 40 and second lingual electrode 40, i.e. at the lingual side of tooth 100, and further aid and expedite bone deposition in the vicinity of each of first buccal electrode 50 and second buccal electrode 50, i.e. at the buccal side of tooth 100. As a result, the bone resorption and deposition caused by the orthodontic appliance is enhanced and expedited by the bone resorption and deposition caused by the generated first and second orthogonal currents, thereby expediting the movement of tooth 100.

In the event that tooth 100 needs to be moved buccally, i.e. away from the tongue, a third and a fourth orthogonal current are generated. Particularly, the third orthogonal current is arranged to flow from the first buccal electrode 50 to the first lingual electrode 40, along axis 120. The second orthogonal current is arranged to flow from the second buccal electrode 50 to the second lingual electrode 40, along axis 130. As described above in relation to the generated first and second orthogonal currents, the generated third and fourth orthogonal currents aid and expedite the bone resorption on the lingual side of tooth 100 and the bone deposition of the buccal side of tooth 100.

In the event that tooth 100 needs to be moved along the gum line of alveolar bone 70, a first and second parallel current is generated. The term 'parallel current' as used herein means that the current flows in a direction generally parallel to the gum line of alveolar bone 70 in the vicinity of tooth 100. The first parallel current is arranged to flow from the first lingual electrode 40 to the second lingual electrode 40 and the second parallel current is arranged to flow from the first buccal electrode 50 to the second buccal electrode 50. As described above in relation to the generated orthogonal currents, the generated first and second parallel currents aid and expedite the bone resorption on the side of tooth 100 in the direction that tooth 100 is being moved to and the bone deposition on the side of tooth 100 where tooth 100 is being moved from.

In the event that tooth 100 needs to be rotated, in one embodiment opposing orthogonal currents are generated. Particularly, an orthogonal current flowing in a lingual direction, i.e. towards the tongue, is arranged to flow from the first buccal electrode 50 to the first lingual electrode 40. Additionally, an orthogonal current flowing in a buccal direction, i.e. away from the tongue, is arranged to flow from the second lingual electrode 40 to the second buccal electrode 50. As illustrated in FIG. 2C, a rotation of tooth 100 in a rotational direction 140 can be viewed as movement of a first side 150 of tooth 100 in a buccal direction 160 and movement of a second side 170 of tooth 100, opposing first side 150, in a lingual direction 180. As illustrated, axis 120 extends through first lingual electrode 40 and first buccal electrode 50 and axis 130 extends through second lingual electrode 40 and second buccal electrode 50. Therefore, the orthogonal current flowing from first buccal electrode 50 to first lingual electrode 40 aids and expedites the bone resorption at the buccal end of first side 150 of tooth 100 and the bone deposition at the lingual end of first side 150 of tooth 100. Additionally, the orthogonal current flowing from second lingual electrode 40 to second buccal electrode 50 aids and expedites the bone resorption at the lingual end of second side 170 of tooth 100 and the bone deposition at the buccal end of second side 170 of tooth 100. In another embodiment, opposing parallel current are generate each between the respective pair of lingual electrodes 40 and buccal electrodes 50. In one embodiment, the magnitude of each the above described orthogonal and parallel current is about 20 micro-amperes.

Providing a lingual electrode 40 and a buccal electrode 50 on each side of tooth 100 thus allows for resorption and deposition simultaneously on both sides of tooth 100. In the event that tooth 100 needs to be tipped, i.e. rotated about any rotation axis extending through the middle of the root of tooth 100, the crown of tooth 100 moves in a first direction while the bottom of the root of tooth 100 moves in an opposing direction. As a result, bone resorption and deposition occurs simultaneously on both sides of the center of rotation. The arrangement of vestibular electronic orthodontic appliance expediter 10 thus allows for enhancement of tipping motion of a tooth 100.

Thus, each tooth 100 can be separately treated responsive to the orthodontic appliance, the movement of each tooth 100 expedited responsive to the respectively generated orthogonal and/or parallel currents. Advantageously, vestibular electronic orthodontic appliance expediter 10 provides a comprehensive system for expediting orthodontic tooth adjustment in any of a plurality of treatment situations, including a combination of bodily and tipping movement of a plurality of teeth 100. Particularly, each of the generated orthogonal currents and parallel current are separately controlled by control circuitry 20. As a result, for each lingual electrode 40 and buccal electrode 50, control circuitry 20 will control whether a parallel current or an orthogonal current will be generated thereat and whether the particular electrode will act as an anode, i.e. outputting the current, or as a cathode, i.e. receiving the current.

Figure 2D:
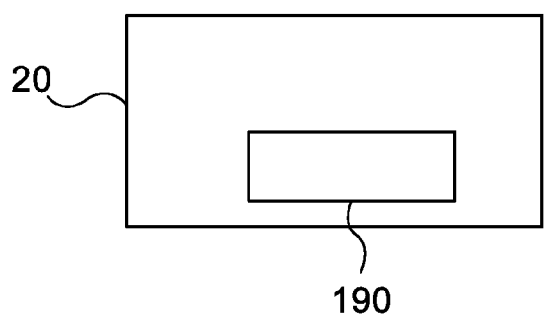

As illustrated in FIG. 2D, control circuitry 20 optionally comprises a user input module 190. User input module 190 is arranged to receive user input, optionally via a connection to an external computer. In one embodiment, user input module 190 is arranged to receive a current polarity selection user input. The directions of the above described generated orthogonal and parallel currents are responsive to the received current polarity selection user input. In another embodiment, user input module 190 is arranged to receive an electrode user input. Control circuitry 20 is arranged to select which lingual electrodes 40 and which buccal electrodes 50 are to be activated for generating and receiving current responsive to the received electrode user input. Particularly, if only several teeth 100 need adjusting, only electrodes associated with those teeth 100 are utilized. In one embodiment, the magnitude of the generated currents can be adjusted via user input module 190.

In one embodiment, control circuitry 20 is arranged to generate the respective orthogonal and parallel currents for a predetermined active duration. Following the predetermined active duration, control circuitry 20 is arranged to not generate the respective orthogonal and parallel currents for a predetermined quiescent duration. Optionally, the predetermined active duration is 3-5 hours and the predetermined quiescent duration is 19-21 hours. Advantageously, generating the respective orthogonal and parallel currents for only a fraction of the day avoids damage to gums 80 from too much electrical stimulation. Clinical research has shown that an active duration of up to 5 hours a day does not cause irritation of gums 80, while an active duration of less than 3 hours a day does not effectively enhance orthodontic tooth movement. In one embodiment, the predetermined active duration and/or the predetermined quiescent duration can be adjusted via user input module 190.

FIGS. 3A-3D illustrate various high level perspective views of a vestibular electronic orthodontic appliance expediter 200. Vestibular electronic orthodontic appliance expediter 200 is in all respects similar to vestibular electronic orthodontic appliance expediter 10, described above, with the exception that vestibular electronic orthodontic appliance expediter 200 further comprises: a lingual member 210; and a buccal member 250. In one embodiment, lingual member 210 and buccal member 250 are portions of a single contiguous member comprising the vestibular electronic orthodontic appliance expediter 200. In another embodiment, lingual member 210 and buccal member 250 are each comprised of plastic. In a first vestibular electronic orthodontic appliance expediter 200, illustrated in FIGS. 3A-3B, lingual member 210 and buccal member 250 are arranged to fit the upper portion of the mouth. Optionally, first vestibular electronic orthodontic appliance expediter 200 further comprises a structural support member 290 arranged to provide structural support for lingual member 210. In a second vestibular electronic orthodontic appliance expediter 200, illustrated in FIGS. 3C-3D, lingual member 210 and buccal member 250 are arranged to fit the lower portion of the mouth.

The plurality of lingual electrodes 40 are disposed on lingual member 210 and the plurality of buccal electrodes 50 are disposed on buccal member 250. Lingual member 210 is arranged to fit the contour of gum 80 over lingual side 60 of alveolar bone 70 such that lingual electrodes 40 are positioned between teeth 100 and buccal member 250 is arranged to fit the contour of gum 80 over buccal side 65 of alveolar bone 70 such that buccal electrodes 50 are positioned between teeth 100, as described above in relation to vestibular electronic orthodontic appliance expediter 10. Control circuitry 20, power source 30 and electrical paths 35 are disposed on lingual member 210 and buccal member 250. Optionally, power source 30 and electrical paths 35 are sealed within cavities, each between two layers of laminated plastic (not shown), thus being isolated from the oral environment. Advantageously, the isolation from the oral environment keeps the electronics of vestibular electronic orthodontic appliance expediter 200 protected from the oral environment and keeps the oral environment protected from any toxicity of the electronics of vestibular electronic orthodontic appliance expediter 200. In one embodiment, the cavities each comprise a vacuum.

As described above, in one embodiment power supply 30 is rechargeable. In such an embodiment, vestibular electronic orthodontic appliance expediter 200 is arranged to fit on a rechargeable power source. Optionally, power supply power 30 is arranged to be charged wirelessly via an inductive coil. Additionally, in one embodiment, during orthodontic treatment vestibular electronic orthodontic appliance expediter 200 is arranged to be placed on a base plate (not shown) and power supply 30 is arranged to inductively receive power from the base plate. As a result, the power stored in power supply 30 won't be wasted during the orthodontic treatment which may utilize increased amounts of power to adjust treatment parameters via control circuitry 20 and/or to detect appropriate conductivity between associated ones of lingual electrodes 40 and buccal electrodes 50, as will be described below in relation to vestibular electronic orthodontic appliance expediter 300.

Figure 7:
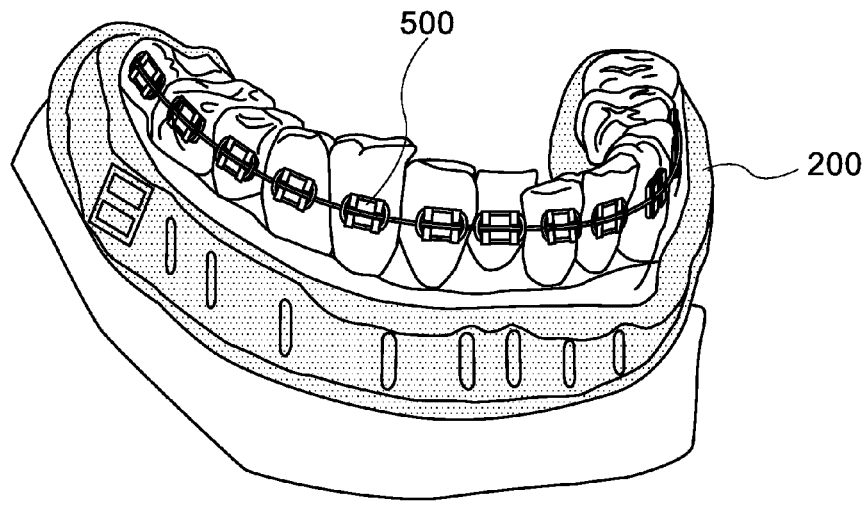
FIG. 7 illustrates a high level view of an exemplary vestibular electronic orthodontic appliance expediter in cooperation with an orthodontic appliance.

Preferably, vestibular electronic orthodontic appliance expediter 200 is arranged to operate in cooperation with any standard orthodontic appliance 500, including: fixed appliances, such as lingual or buccal braces; and removal aligners, such as the Invisalign clear aligner commercially available from Align Technology Inc. of San Jose, Calif. as illustrated in FIG. 7.

Figure 3A:
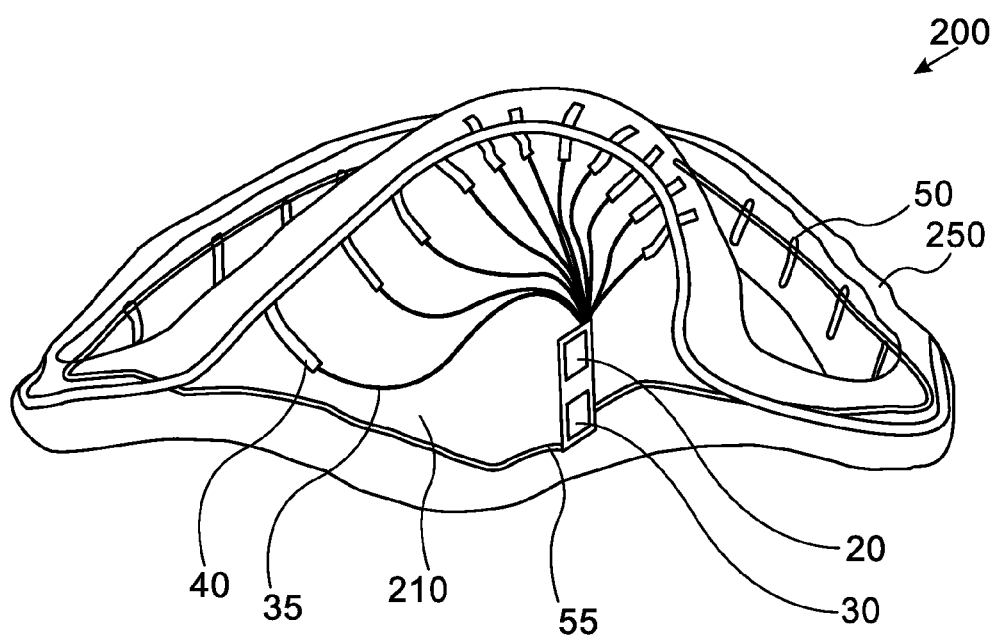
FIGS. 3A-3D illustrate various high level views of a second embodiment of an vestibular electronic orthodontic appliance expediter, according to certain embodiments.
Figure 3B:
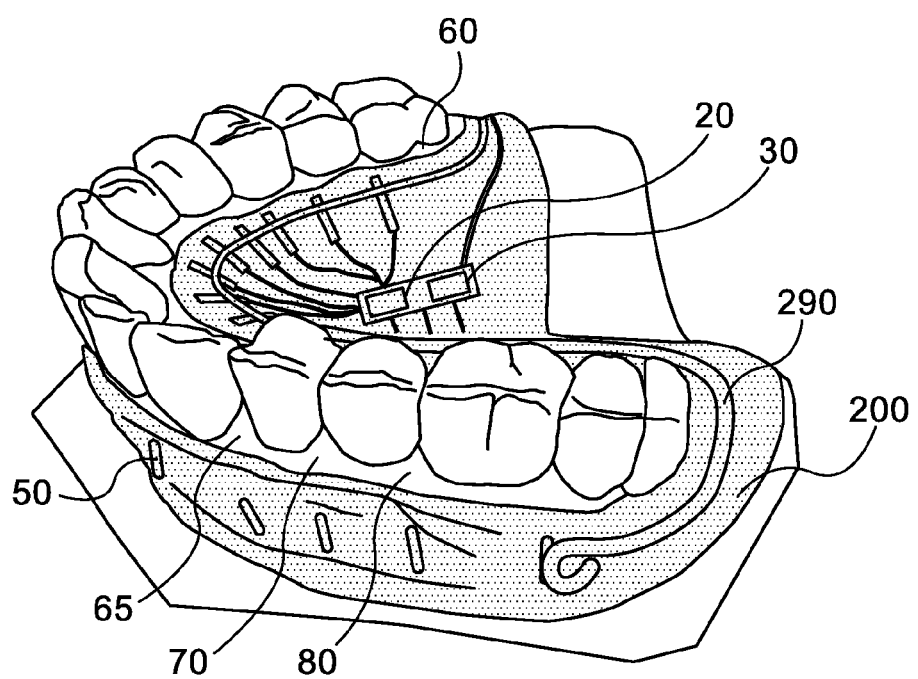
Figure 3C:
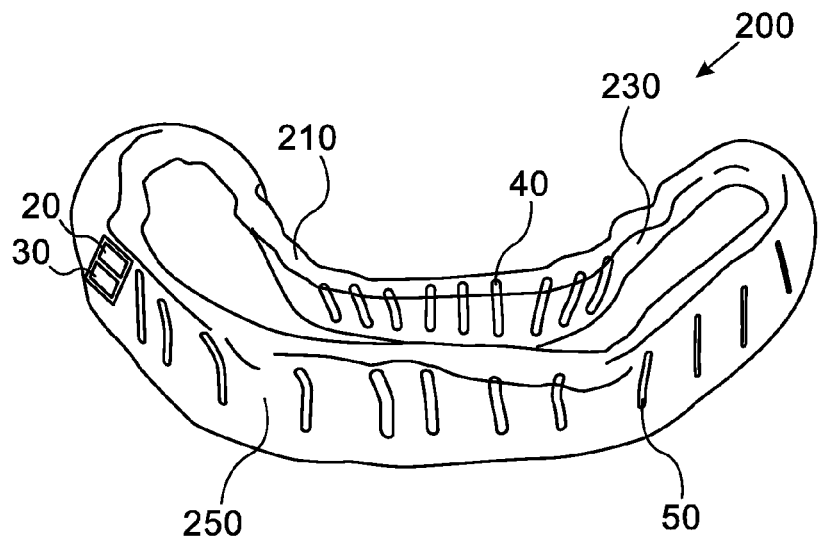
Figure 3D:
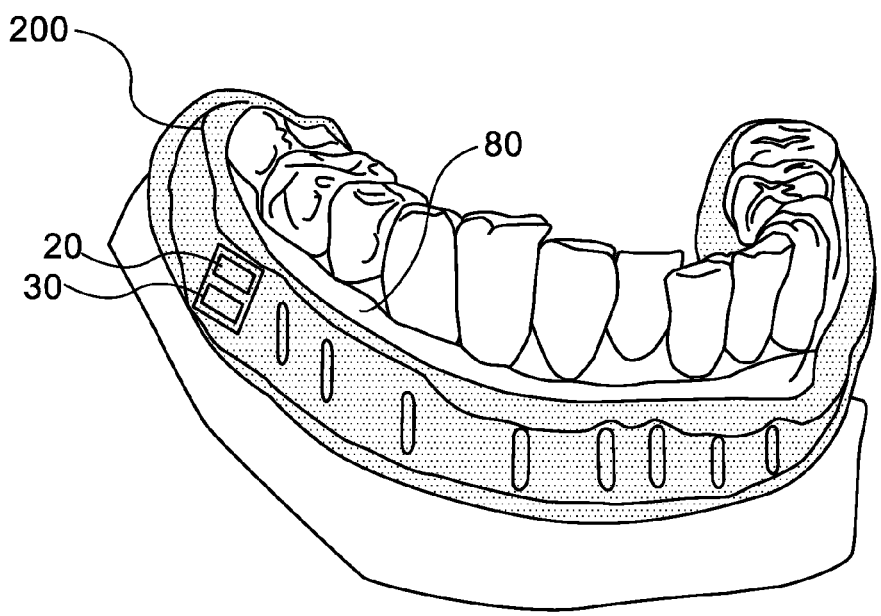

As shown in FIG. 3C, in one embodiment vestibular electronic orthodontic appliance expediter 200 is arranged as a flexible Mobius strip which as shown in FIG. 7 may be placed orally without interfering with prior art orthodontic appliance 500. In one embodiment, vestibular electronic orthodontic appliance expediter 200 is shaped such as to be completely tissue borne, without contacting surfaces of any teeth in the patient.

Figure 8:
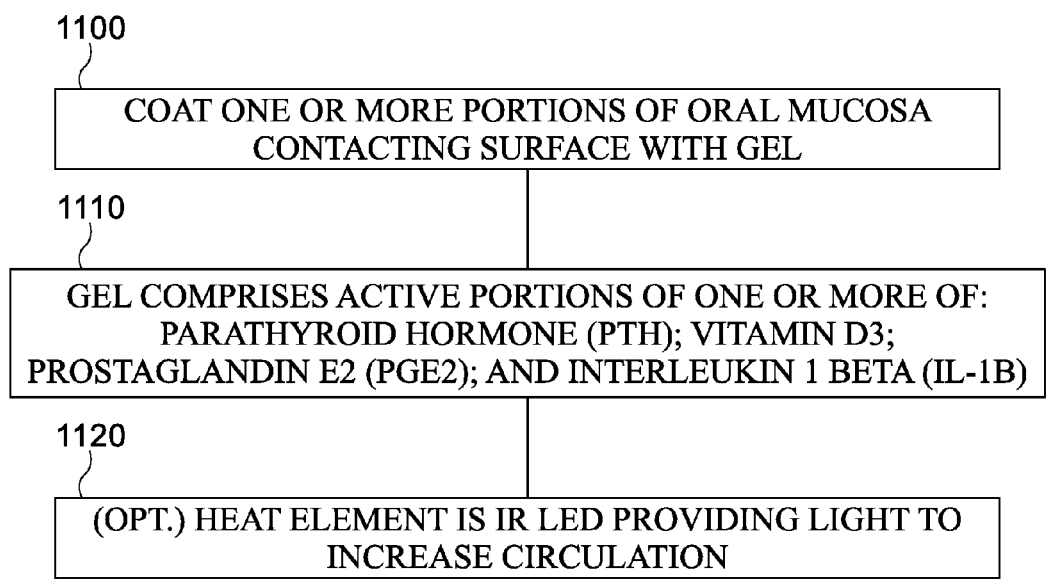
FIG. 8 illustrates a high level flow chart of a method of providing trans-mucosal administration of chemical entities in cooperation with a vestibular electronic orthodontic appliance expediter, according to certain embodiments.

It is known that the pH of the oral cavity offers relatively consistent and friendly physiological conditions for drug delivery, which are maintained by the continual secretion of saliva. Compared to secretions of the GI tract, saliva is a relatively mobile fluid with less mucin, limited enzymatic activity and virtually no proteases. Thus, in one embodiment, one or more portions of surface 230 of vestibular electronic orthodontic appliance expediter 200 which are in contact with oral mucosa of the patient, are coated with a layer of a gel preparation, containing molecules participating regularly in the inflammatory process that is the biological basis of orthodontic tooth movement, as described in stage 1100 of FIG. 8. As described in stage 1110, the gel may comprise one or more of: parathyroid hormone (PTH); vitamin D3; prostaglandin E2 (PGE2); and interleukin 1 beta (IL-1β). The gel is in one embodiment painted over the oral mucosa side of the device by a practitioner at regular intervals, or by the patient every day, prior to inserting the device into the mouth.

Inclusion of PTH, vitamin D3, PGE2 and/or IL-1β in the applied gel is based upon discoveries pertaining to their pivotal roles in bone remodeling, and their ability to generate synergistic responses by their target cells in inflamed tissues. However, these molecules may be too large for trans-mucosal passage. In that case it may be reasonable to utilize only the active sections of the molecules. For PTH it is the 1-84 segment, the one with the N terminal, with a half-life time of only 5 minutes. The gel applied to surface 230 can contain one or all of these molecules. Research has demonstrated that achieving synergistic effects requires very low concentrations of each of the involved molecules. Vitamin D3 is a hormonal regulator of calcium metabolism in the body, and as such is involved in bone apposition and resorption. The application of minute electric currents to the same tissues during orthodontic treatment may augment the passage of the inflammatory molecules through the oral mucosa.

In one embodiment, vestibular electronic orthodontic appliance expediter 200 can further be utilized to expedite bone filling of tooth extraction sites. Particularly, when a tooth is extracted and no implant is provided for replacing the extracted tooth, the extraction site is left empty. Preferably, bone growth is desired to fill in the empty extraction site. The currents generated by lingual electrodes 40 and buccal electrodes 50 will aid in the deposition of bone in the empty extraction site. Particularly, parallel currents are received by each of the lingual electrodes 40 and buccal electrodes 50 associated with the tooth extraction site, the parallel currents received from adjacent lingual electrodes 40 and buccal electrodes 50. As described above, bone deposition occurs at an electrode which receives current. In another embodiment, where an implant is inserted, the current generated by lingual electrodes 40 and buccal electrodes 50 will aid in the formation of bone around the implant. In one embodiment, alveolar bone loss caused by dentures can be reversed responsive to bone deposition caused by generated parallel currents, as described above. In another embodiment, periodontal bone defects can be repaired responsive to bone deposition caused by generated parallel currents, as described above.

Vestibular electronic orthodontic appliance expediter 200 thus advantageously provides a comprehensive device, adaptive for a plurality of orthodontic patients. Particularly, as described above, a plurality of parallel and/or orthogonal current can be generated, as required for the particular patient's needs. Additionally, as described above, the currents can be adjusted, and/or new currents may be generated in accordance with the orthodontic treatment process.

Figure 4:
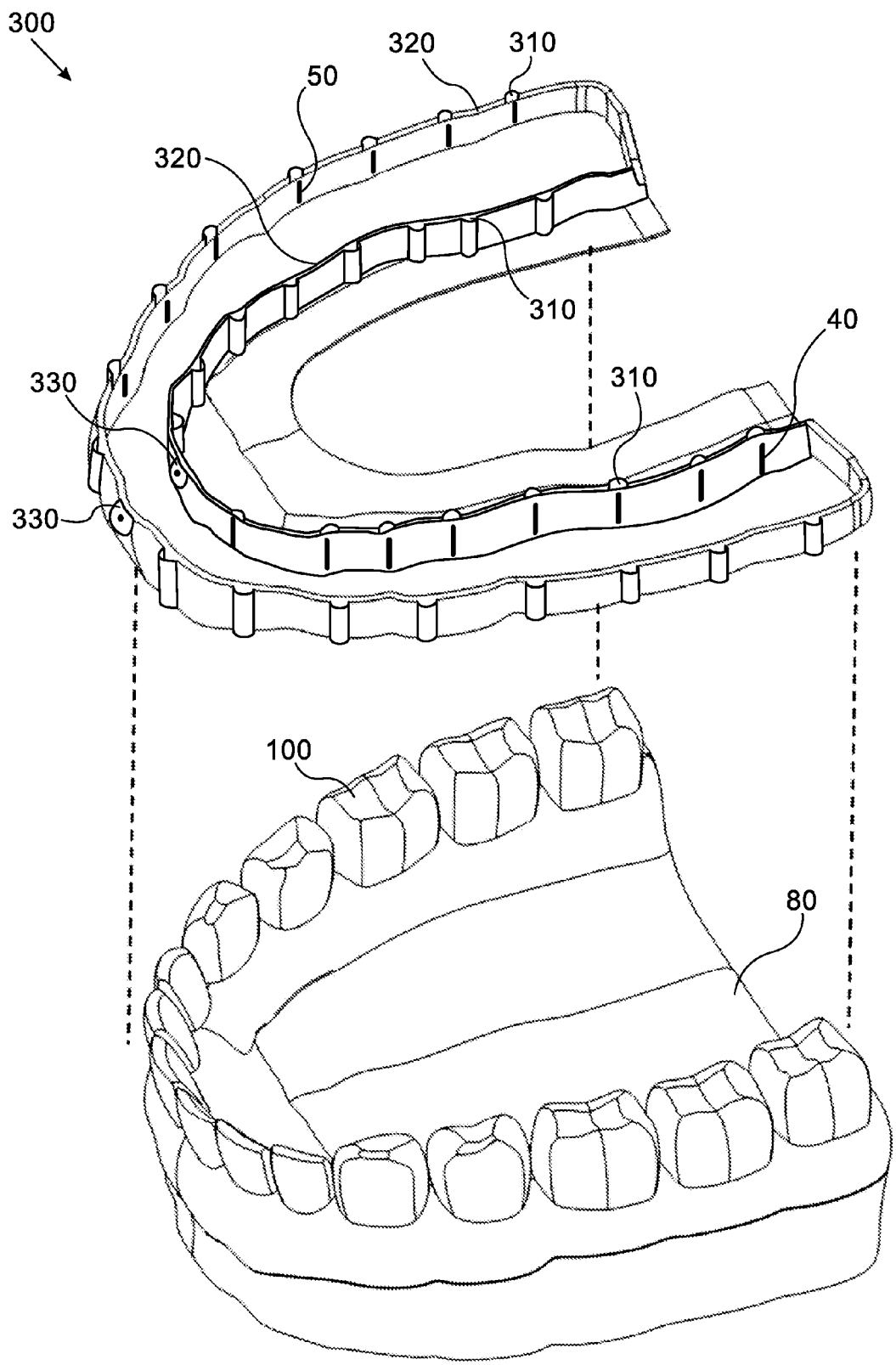
FIG. 4 illustrates a high level perspective view of a third embodiment of an vestibular electronic orthodontic appliance expediter, according to certain embodiments.

FIG. 4 illustrates a high level perspective open view of an vestibular electronic orthodontic appliance expediter 300. Vestibular electronic orthodontic appliance expediter 300 is in all respects similar to vestibular electronic orthodontic appliance expediter 200 with the exception that vestibular electronic orthodontic appliance expediter 300 further comprises a plurality of adjustable pressure elements 310. Each adjustable pressure element 310 is juxtaposed with a respective one of lingual electrodes 40 and buccal electrodes 50. In one embodiment, each adjustable pressure element 310 comprises a flexible tubule. During the treatment process, as teeth 100 begin to move into the desired positions, the contact between lingual electrodes 40 and gum 80, and the contact between buccal electrodes 50 and gum 80 may become less optimal due to the movement of teeth 100. In one embodiment, air is pumped into each adjustable pressure element 310 thereby expanding the flexible tubule and applying pressure to the respective lingual electrodes 40 and buccal electrodes 50. Responsive to the applied pressure, the respective lingual electrodes 40 and buccal electrodes 50 are pushed against gum 80, thereby improving the contact therewith. Optionally, as illustrated, adjustable pressure elements 310 are attached to a common air channel 320, air being added to adjustable pressure elements 310 via common air channel 320. Alternatively, a particular gas may be used instead of air. Optionally, common air channel 320 exhibits a unidirectional opening 330, air being injected into common air channel 320 via unidirectional opening 330. In another embodiment, a solid pressure member is inserted into each adjustable pressure element 310, the flexible tubule thereof expanding responsive to the inserted pressure member and applying pressure to the respective lingual electrodes 40 and buccal electrodes 50. Optionally, a plurality of pressure members are provided, with a range of diameters, each thus providing a different amount of pressure to the respective one of lingual electrodes 40 and buccal electrodes 50.

In the embodiment where the pressure is adjusted by air, adjustable pressure elements 310 and common air channels 320 are enclosed between two layers of laminated plastic (not shown) to keep air from escaping vestibular electronic orthodontic appliance expediter 300. Additionally, adjustable pressure elements 310 and common air channels 320 are closed to keep air from escaping.

In one embodiment, control circuitry 20 is arranged to measure the conductivity, or impedance, between each pair of lingual electrodes 40 and buccal electrodes 50. Particularly, an orthogonal current is generated between each lingual electrode 40 and the associated buccal electrode 50, responsive to the voltage potentials thereat. Alternately, a parallel current is generated between adjacent lingual electrodes 40 and between adjacent buccal electrodes 50. Control circuitry 20 is arranged to measure the magnitude of the generated current and optionally calculate the resistance, or conductivity, between the electrodes. The amount of pressure applied to each lingual electrode 40 and buccal electrode 50 is adjusted to arrive at the desired predetermined resistance or conductivity.

Figure 5:
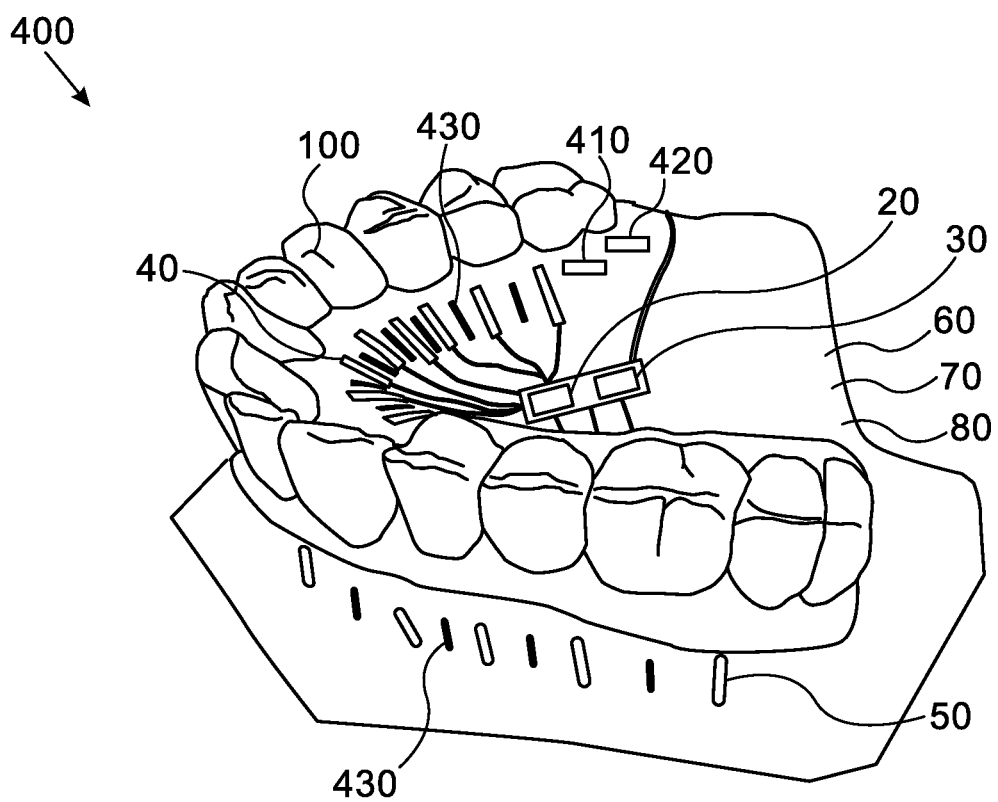
FIG. 5 illustrates a perspective view of a fourth embodiment of an vestibular electronic orthodontic appliance expediter.

FIG. 5 illustrates a perspective view of a fourth embodiment of an vestibular electronic orthodontic appliance expediter 400. Vestibular electronic orthodontic appliance expediter 400 is in all respects similar to vestibular electronic orthodontic appliance expediter 10 of FIGS. 2A-2B, with the addition of a temperature sensor 410, a pH sensor 420 and a plurality of heating elements 430, each in communication with control circuitry 20 (connections not shown). In one embodiment, each heating element 430 comprises an infrared (IR) light emitting diode (LED) 430, and is described herein as such. In one embodiment, each of the plurality of IR LEDs 430 is positioned between a respective pair of lingual electrodes 40 or buccal electrodes 50. Temperature sensor 410 and pH sensor 420 are illustrated as being positioned on gum 80 of lingual side 60 of alveolar bone 70, however this is not meant to be limiting in any way. Utilization of LEDs for the heating element, and preferably IR LEDs for the heating element, is further advantageous in that the LED provides light to the gums of the alveolar bone to at least temporarily increase blood circulation.

In operation, temperature sensor 410 is arranged to sense the temperature in the vicinity of teeth 100. Additionally, pH sensor 420 is arranged to sense the pH level in the vicinity of teeth 100. Control circuitry 20 is arranged to enable IR LEDs 430 to heat gums 80 responsive to the sensed temperature of temperature sensor 410. Particularly, control circuitry 20 is arranged to analyze the output of temperature sensor 410 and determine an average baseline temperature in the vicinity of teeth 100. IR LEDs 430 are arranged to raise the temperature 1-2 degrees above the determined average baseline temperature which will enhance the inflammatory response of gums 80, thereby enhancing the osteogenesis response during movement of teeth 100. Temperature sensor 410 is used by control circuitry 20 as a feedback mechanism to ensure that the temperature in the vicinity of teeth 100 is maintained within a predetermined range.

Control circuitry 20 is further arranged to control power source 30 to adjust the amplitude of the generated currents responsive to the sensed pH level. The generated currents can cause a reduction in the pH level due to an electrolytic effect around lingual electrodes 40 and buccal electrodes 50. In the event that the pH level drops below a predetermined value, the current magnitude is reduced so as to avoid excessive acidity gums 80 which can damage teeth 100.

Figure 6A:
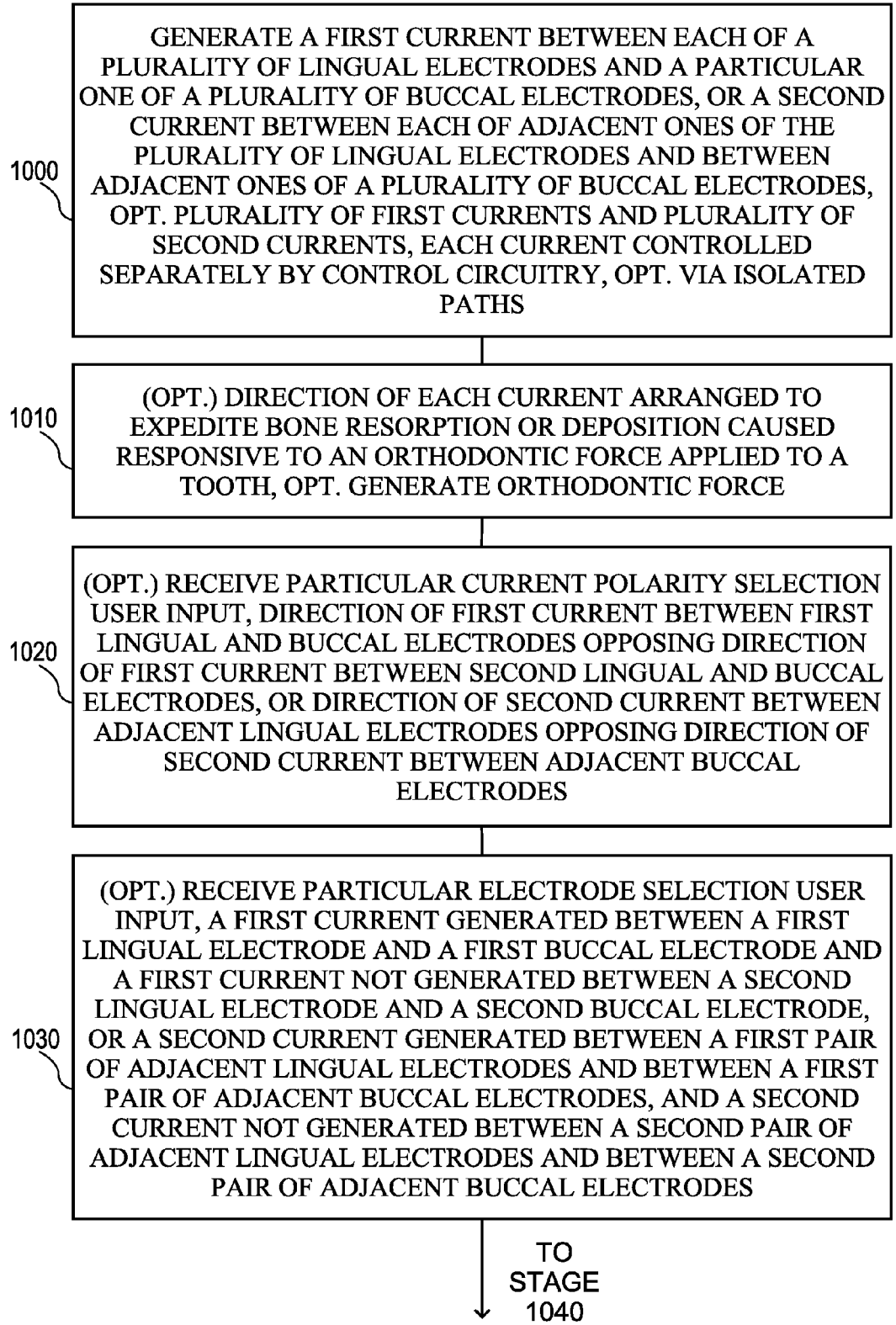
FIGS. 6A-6B illustrate a high level flow chart of a method of expediting orthodontic tooth adjustment, according to certain embodiments.
Figure 6B:
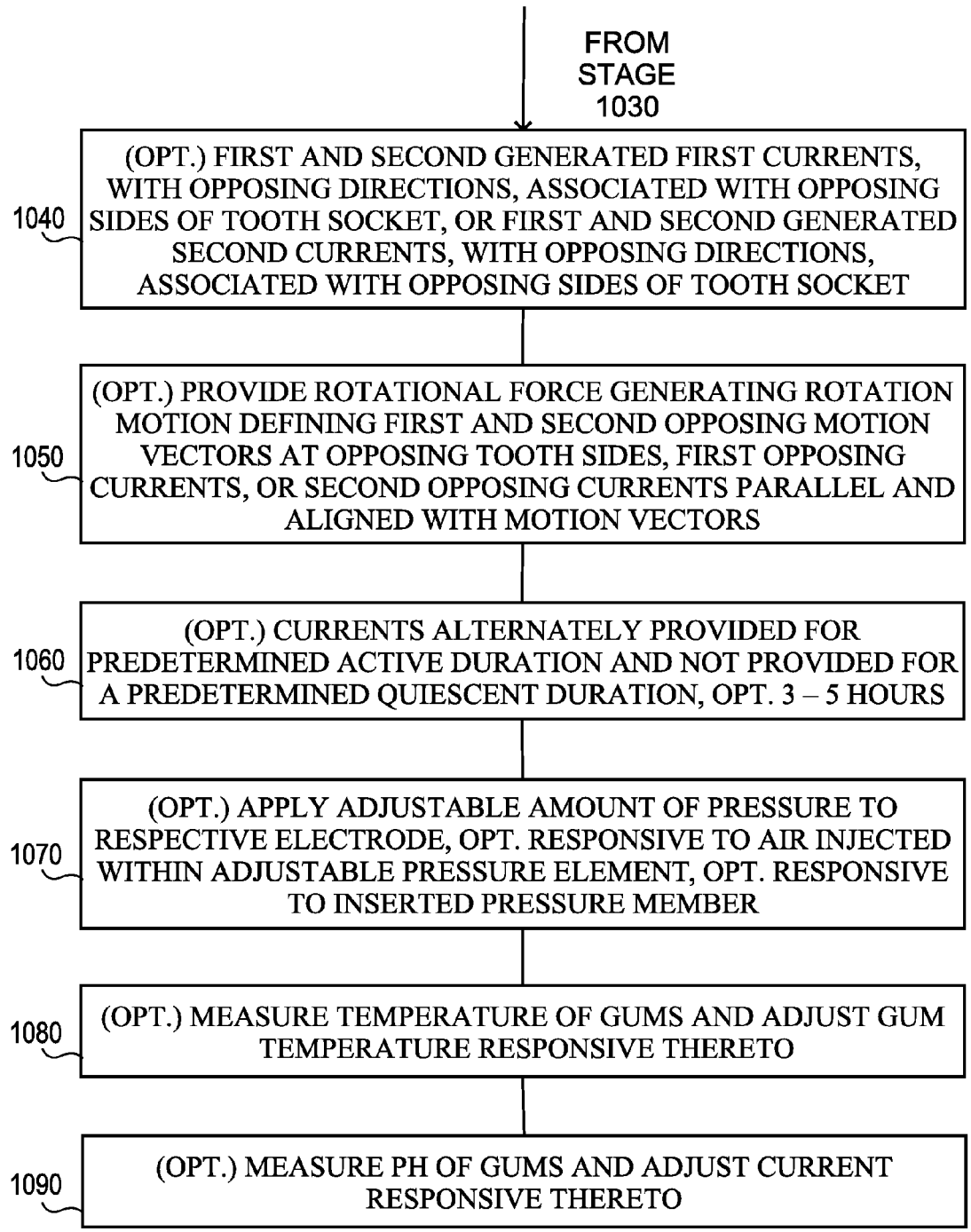

FIGS. 6A-6B illustrate a high level flow chart of a method of expediting orthodontic tooth adjustment. In stage 1000, a first type current is generated between each of a plurality of lingual electrodes and a particular one of a plurality of buccal electrodes, as described above in relation to the generated orthogonal currents. Alternately, or additionally, a second type current is generated between each of adjacent ones of the plurality of lingual electrodes and between adjacent ones of the plurality of buccal electrodes, as described above in relation to the generated parallel currents. Optionally, a plurality of first type currents, each between a particular lingual electrode and a particular buccal electrode, and a plurality of second type currents, each between adjacent lingual electrodes or adjacent buccal electrodes, are generated. As described above, a lingual electrode is positioned between each tooth on the lingual side of the alveolar bone and a buccal electrode is positioned between each tooth on the buccal side of the alveolar bone. Each of the generated first and second type currents is controlled separately by a control circuitry. Optionally, each of the lingual and buccal electrodes is in communication with the control circuitry via a respective one of a plurality of electrical paths, isolated from the rest of the plurality of electrical paths. As will be described below, the control circuitry is arranged to control the magnitude and direction of each generated current.

In optional stage 1010, the direction of each generated current of stage 1000 is arranged so as to expedite bone resorption and/or deposition caused responsive to an orthodontic force applied to a tooth disposed within the respective tooth socket associated with the respective electrodes generating the current. Further optionally, the orthodontic force is generated by an orthodontic appliance.

In optional stage 1020, a particular current polarity selection user input is received. Responsive to the received current polarity selection user input, the direction of a generated first type current of stage 1000 between a first lingual electrode and a first buccal electrode opposes the direction of a generated first type current between a second lingual electrode and a second buccal electrode. Alternatively, or additionally, responsive to the received current polarity selection user input, the direction of a generated second type current of stage 1000 between adjacent lingual electrodes opposes the direction of a generated second type current between adjacent buccal electrodes. Particularly, the direction of each generated current is selected responsive to a user input, thereby allowing flexibility for a wide range of tooth movements, as described above.

In optional stage 1030, a particular electrode selection user input is received. Responsive to the received electrode selection user input, a first type current of stage 1000 is generated between a first lingual electrode and a first buccal electrode and another first type current is not generated between a second lingual electrode and a second buccal electrode. Alternatively, or additionally, a second type current of stage 1000 is generated between a first pair of adjacent lingual electrodes and between a first pair of adjacent buccal electrodes, and another second type current is not generated between a second pair of adjacent lingual electrodes and between a second pair of adjacent buccal electrodes. Particularly, the number of generated first and second type currents is selected responsive to a user input.

In optional stage 1040, a first and a second first type currents, exhibiting opposing directions, are generated. Each of the first type currents, i.e. orthogonal currents, is associated with an opposing side of a tooth socket. Alternatively, or additionally, a first and a second second type currents, exhibiting opposing direction, are generated. Each of the second type currents, i.e. parallel currents, is associated with an opposing side of a tooth socket. In optional stage 1050, an orthodontic rotational force is provided by an orthodontic appliance, the orthodontic rotational force generating rotational motion of a tooth. The rotational motion defines a first and a second opposing motion vectors at opposing sides of the tooth. The opposing first type currents, or second type currents, of optional stage 1040 are each generally parallel and aligned with a respective one of the motion vectors.

In optional stage 1060, the generated currents of stage 1000 are alternately provided for a predetermined active duration and not provided for a predetermined quiescent duration. Optionally, the predetermined active duration is 3-5 hours and the predetermined quiescent duration is 19-21 hours.

In optional stage 1070, an adjustable amount of pressure is applied to each of the plurality of lingual and buccal electrodes of stage 1000. Optionally, the adjustable amount of pressure is applied responsive to air being injected into a flexible tubule, the tubule expanding responsive to the injected air and applying pressure to an associated electrode.

Optionally, the adjustable amount of pressure is applied responsive to a pressure member being inserter into each of the plurality of flexible tubules, the tubule expanding responsive to the inserted pressure member and applying pressure to the associated electrode.

In optional stage 1080, the temperature of the gums is sensed by a temperature sensor and the temperature of the gums is adjusted responsive to the sensed temperature. In one embodiment, the gums are heated by a pluraltiy of IR LEDs to 1-2 degrees above an average baseline temperature of the gums. As described above, heating the gums enhances the inflammatory response of the gums, thereby enhancing the osteogenesis response during movement of the teeth.

In optional stage 1090, the pH level of the gums is sensed by a pH sensor and the magnitude of the generated first current, or second current, of stage 1000 is adjusted responsive to the sensed pH level. Particularly, in the event that the pH level is below a predetermined first value, the magnitude of the current is reduced, and if the pH is above a predetermined second value, the magnitude of the current is increased. As a result of optional stage 1090, the pH level is actively maintained to be within a predetermined range between the first and second values.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

Unless otherwise defined, all technical and scientific terms used herein have the same meanings as are commonly understood by one of ordinary skill in the art to which this invention belongs. Although methods similar or equivalent to those described herein can be used in the practice or testing of the present invention, suitable methods are described herein.

All publications, patent applications, patents, and other references mentioned herein are incorporated by reference in their entirety. In case of conflict, the patent specification, including definitions, will prevail. In addition, the materials, methods, and examples are illustrative only and not intended to be limiting.

The terms "include", "comprise" and "have" and their conjugates as used herein mean "including but not necessarily limited to".

It will be appreciated by persons skilled in the art that the present invention is not limited to what has been particularly shown and described hereinabove. Rather the scope of the present invention is defined by the appended claims and includes both combinations and sub-combinations of the various features described hereinabove as well as variations and modifications thereof, which would occur to persons skilled in the art upon reading the foregoing description.

The invention claimed is:

1. A vestibular electronic orthodontic appliance expediter comprising:
    a lingual sub-member and a buccal sub-member, said lingual sub-member arranged to fit a lingual contour of a gum of a patient over a lingual side of an alveolar bone of the patient, said buccal sub-member arranged to fit a buccal contour of a gum of the patient over a buccal side of the alveolar bone;
    a control circuitry;
    a plurality of lingual electrodes disposed on said lingual sub-member, each of said plurality of lingual electrodes adapted to be juxtaposed with a respective one of a plurality of tooth sockets within the alveolar bone; and
    a plurality of buccal electrodes disposed on said buccal sub-member, each of said plurality of buccal electrodes adapted to be juxtaposed with a respective one of the plurality of tooth sockets within the alveolar bone,
    wherein said control circuitry is arranged to generate, via said plurality of lingual electrodes and said plurality of buccal electrodes at least one of:
        a plurality of orthogonal currents, each controlled separately responsive to said control circuitry; and
        a plurality of parallel currents, each controlled separately responsive to said control circuitry,
    wherein each of said plurality of orthogonal currents is generated between a respective one of said plurality of lingual electrodes and a respective one of said plurality of buccal electrodes, said respective ones associated with the same respective tooth socket,
    wherein each of said plurality of parallel currents is generated between one of:
        a respective one of said plurality of lingual electrodes and one of said plurality of lingual electrodes adjacent thereto; and
        a respective one of said plurality of buccal electrodes and one of said plurality of buccal electrodes adjacent thereto, and
    wherein the vestibular electronic orthodontic appliance expediter is shaped such as to be completely tissue borne.

2. The vestibular electronic orthodontic appliance expediter of claim 1, wherein said lingual sub-member and a buccal sub-member are formed into a single contiguous member.

3. The vestibular electronic orthodontic appliance expediter of claim 2, wherein said control circuitry is disposed within said single contiguous member.

4. The vestibular electronic orthodontic appliance expediter of claim 1, wherein said control circuitry is arranged to control the direction of each of said generated currents to expedite bone resorption or deposition caused responsive to an orthodontic force applied to a tooth disposed within the respective tooth socket by an orthodontic appliance.

5. The vestibular electronic orthodontic appliance expediter of claim 1, further comprising a plurality of electrical paths isolated from each other, said control circuitry in electrical communication with each of said plurality of lingual electrodes, or with each of said plurality of buccal electrodes, via a respective one of said plurality of electrical paths.

6. The vestibular electronic orthodontic appliance expediter of claim 1, wherein said control circuitry comprises a user input module arranged to receive a current polarity selection user input,
    wherein responsive to a particular current polarity selection user input received at said user input module, said control circuitry is arranged to control the direction of said generated orthogonal current between a first of said plurality of lingual electrodes and a first of said plurality of buccal electrodes to oppose the direction of said generated orthogonal current between a second of said plurality of lingual electrodes and a second of said plurality of buccal electrodes,
    and wherein said control circuitry is arranged to control the direction of said generated parallel current between a pair of adjacent ones of said plurality of lingual electrodes to oppose the direction of said generated parallel current between a pair of adjacent ones of said plurality of buccal electrodes.

7. The vestibular electronic orthodontic appliance expediter of claim 1, wherein said control circuitry comprises a user input module arranged to receive an electrode selection user input,
wherein responsive to a particular electrode selection user input received at said user input module, said control circuitry is arranged to generate said plurality of orthogonal currents between a first set of said plurality of lingual electrodes and a first set of said plurality of buccal electrodes, and not generate an orthogonal current between a second set of said plurality of lingual electrodes and a second set of said plurality of buccal electrodes.

8. The vestibular electronic orthodontic appliance expediter of claim 1, wherein said control circuitry is arranged to alternately provide said generated currents for a predetermined active duration and not provide said generated currents for a predetermined quiescent duration, said predetermined active duration being 3-5 hours.

9. The vestibular electronic orthodontic appliance expediter of claim 1, further comprising:
a temperature sensor arranged to sense the temperature of the gums of the alveolar bone; and
a heating element arranged to heat the gums of the alveolar bone, responsive to said sensed temperature.

10. The vestibular electronic orthodontic appliance expediter of claim 1, further comprising a pH sensor arranged to sense the pH level of the gums of the alveolar bone,
wherein said control circuitry is arranged to adjust the magnitude of said plurality of at least one of orthogonal currents and parallel currents responsive to said sensed pH level.

11. The vestibular electronic orthodontic appliance expediter of claim 1, wherein at least a portion of an oral mucosa facing surface of one of said lingual sub-member and said buccal sub-member is coated with a gel comprising an active section of molecules from one of: parathyroid hormone; prostaglandin E2 (PGE2); and interleukin 1 beta (IL-1 β).

12. The vestibular electronic orthodontic appliance expediter of claim 1, wherein each of said plurality of lingual electrodes and each of said plurality of buccal electrodes extends from 1 millimeter apical to the gingival margin to the mucogingival junction of the gum.

13. The vestibular electronic orthodontic appliance expediter of claim 1, wherein each of said plurality of lingual electrodes and each of said plurality of buccal electrodes extends from 1 millimeter apical to the gingival margin to at least one millimeter over the mucosal tissue of the gum.

14. The vestibular electronic orthodontic appliance expediter of claim 1, wherein said control circuitry is arranged to generate the plurality of orthogonal currents and the plurality of parallel currents.

15. The vestibular electronic orthodontic appliance expediter of claim 1, wherein a first of said plurality of lingual electrodes is adapted to be juxtaposed with a first side of a particular tooth socket, and a second of said plurality of lingual electrodes is adapted to be juxtaposed with a second side of the particular tooth socket, the second side of the tooth socket opposing the first side of the tooth socket,
wherein a first of said plurality of buccal electrodes is adapted to be juxtaposed with the first side of the particular tooth socket, and a second of said plurality of buccal electrodes is adapted to be juxtaposed with the second side of the particular tooth socket, and
wherein said arrangement of said control circuitry to generate said currents comprises an arrangement to generate a first orthogonal current between said first lingual electrode and said first buccal electrode and a second orthogonal current between said second lingual electrode and said second buccal electrode, the direction of said second orthogonal current opposing the direction of said first orthogonal current.

16. The vestibular electronic orthodontic appliance expediter of claim 15, further comprising an orthodontic appliance arranged to provide a rotation force to a tooth having a root within the particular tooth socket, said rotational orthodontic force arranged to generate rotational motion of the tooth, said generated rotation motion defining:
a first motion vector in a first direction at a portion of a first side of the tooth; and
a second motion vector, in a second direction opposing said first direction, at a portion of a second side of the tooth, the second side of the tooth opposing the first side of the tooth;
wherein a first axis extending between said first of said plurality of lingual electrodes and said first of said plurality of buccal electrodes is parallel and aligned with said first motion vector,
wherein a second axis extending between said second of said plurality of lingual electrodes and said second of said plurality of buccal electrodes is parallel and aligned with said second motion vector, and
wherein the direction of said orthogonal current generated between said first of said plurality of lingual electrodes and said first of said plurality of buccal electrodes and the direction of said orthogonal current generated between said second of said plurality of lingual electrodes and said second of said plurality of buccal electrodes are arranged to expedite bone resorption and deposition caused responsive to said provided rotational orthodontic force.

17. The vestibular electronic orthodontic appliance expediter of claim 1, wherein said control circuitry comprises a user input module arranged to receive an electrode selection user input,
wherein responsive to a particular electrode selection user input received at said user input module said control circuitry is arranged to generate:
a first of said plurality of parallel currents between a first pair of adjacent ones of said plurality of lingual electrodes; and
a second of said plurality of parallel currents between a first pair of adjacent ones of said plurality of buccal electrodes,
and not generate a parallel current between at least one of:
a second pair of adjacent ones of said plurality of lingual electrodes; and
a second pair of adjacent ones of said plurality of buccal electrodes.

18. A vestibular electronic orthodontic appliance expediter comprising:
a lingual sub-member and a buccal sub-member, said lingual sub-member arranged to fit a lingual contour of a gum of a patient over a lingual side of an alveolar bone of the patient, said buccal sub-member arranged to fit a buccal contour of a gum of the patient over a buccal side of the alveolar bone;
a control circuitry;
a plurality of lingual electrodes disposed on said lingual sub-member, each of said plurality of lingual electrodes adapted to be juxtaposed with a respective one of a plurality of tooth sockets within the alveolar bone; and
a plurality of buccal electrodes disposed on said buccal sub-member, each of said plurality of buccal electrodes adapted to be juxtaposed with a respective one of the plurality of tooth sockets within the alveolar bone, wherein said control circuitry is arranged to generate a plurality of orthogonal currents and a plurality of parallel currents via said plurality of lingual electrodes and said plurality of buccal electrodes, wherein each of said plurality of orthogonal currents is generated between a respective one of said plurality of lingual electrodes and a respective one of said plurality of buccal electrodes, said respective ones associated with the same respective tooth socket, wherein each of said plurality of parallel currents is generated between one of:
  a respective one of said plurality of lingual electrodes and one of said plurality of lingual electrodes adjacent thereto; and
  a respective one of said plurality of buccal electrodes and one of said plurality of buccal electrodes adjacent thereto, and wherein each of said generated orthogonal currents and each of said generated parallel currents is controlled separately responsive to said control circuitry.

19. The vestibular electronic orthodontic appliance expediter of claim 18, wherein the vestibular electronic orthodontic appliance expediter is shaped such as to be completely tissue borne.

20. The vestibular electronic orthodontic appliance expediter of claim 19, wherein each of said plurality of lingual electrodes and each of said plurality of buccal electrodes extends from 1 millimeter apical to the gingival margin to the mucogingival junction of the gum.

21. The vestibular electronic orthodontic appliance expediter of claim 19, wherein each of said plurality of lingual electrodes and each of said plurality of buccal electrodes extends from 1 millimeter apical to the gingival margin to at least one millimeter over the mucosal tissue of the gum.

22. The vestibular electronic orthodontic appliance expediter of claim 18, wherein a first of said plurality of lingual electrodes is adapted to be juxtaposed with a first side of a particular tooth socket, and a second of said plurality of lingual electrodes is adapted to be juxtaposed with a second side of the particular tooth socket, the second side of the tooth socket opposing the first side of the tooth socket, wherein a first of said plurality of buccal electrodes is adapted to be juxtaposed with the first side of the particular tooth socket, and a second of said plurality of buccal electrodes is adapted to be juxtaposed with the second side of the particular tooth socket, and wherein said arrangement of said control circuitry to generate a plurality of orthogonal currents comprises an arrangement to generate a first orthogonal current between said first lingual electrode and said first buccal electrode and a second orthogonal current between said second lingual electrode and said second buccal electrode, the direction of said second orthogonal current opposing the direction of said first orthogonal current.

23. The vestibular electronic orthodontic appliance expediter of claim 22, further comprising an orthodontic appliance arranged to provide a rotation force to a tooth having a root within the particular tooth socket, said rotational orthodontic force arranged to generate rotational motion of the tooth, said generated rotation motion defining:
  a first motion vector in a first direction at a portion of a first side of the tooth; and
  a second motion vector, in a second direction opposing said first direction, at a portion of a second side of the tooth, the second side of the tooth opposing the first side of the tooth;

wherein a first axis extending between said first of said plurality of lingual electrodes and said first of said plurality of buccal electrodes is parallel and aligned with said first motion vector, wherein a second axis extending between said second of said plurality of lingual electrodes and said second of said plurality of buccal electrodes is parallel and aligned with said second motion vector, and wherein the direction of said orthogonal current generated between said first of said plurality of lingual electrodes and said first of said plurality of buccal electrodes and the direction of said orthogonal current generated between said second of said plurality of lingual electrodes and said second of said plurality of buccal electrodes are arranged to expedite bone resorption and deposition caused responsive to said provided rotational orthodontic force.

24. A vestibular electronic orthodontic appliance expediter comprising:
  a lingual sub-member and a buccal sub-member, said lingual sub-member arranged to fit a lingual contour of a gum of a patient over a lingual side of an alveolar bone of the patient, said buccal sub-member arranged to fit a buccal contour of a gum of the patient over a buccal side of the alveolar bone;
  a control circuitry;
  a plurality of lingual electrodes disposed on said lingual sub-member; and
  a plurality of buccal electrodes disposed on said buccal sub-member, wherein said control circuitry is arranged to generate a plurality of orthogonal currents via said plurality of lingual electrodes and said plurality of buccal electrodes, wherein each of said plurality of orthogonal currents is generated between a respective one of said plurality of lingual electrodes and a respective one of said plurality of buccal electrodes, wherein each of said generated plurality of orthogonal currents is controlled separately responsive to said control circuitry, wherein a first of said plurality of lingual electrodes is adapted to be juxtaposed with a first side of a particular tooth socket, and a second of said plurality of lingual electrodes is adapted to be juxtaposed with a second side of the particular tooth socket, the second side of the tooth socket opposing the first side of the tooth socket, wherein a first of said plurality of buccal electrodes is adapted to be juxtaposed with the first side of the particular tooth socket, and a second of said plurality of buccal electrodes is adapted to be juxtaposed with the second side of the particular tooth socket, and wherein said arrangement of said control circuitry to generate a plurality of orthogonal currents comprises an arrangement to generate a first orthogonal current between said first lingual electrode and said first buccal electrode and a second orthogonal current between said second lingual electrode and said second buccal electrode, the direction of said second orthogonal current opposing the direction of said first orthogonal current.

25. The vestibular electronic orthodontic appliance expediter of claim 24, further comprising an orthodontic appliance arranged to provide a rotation force to a tooth having a root within the particular tooth socket, said rotational orthodontic force arranged to generate rotational motion of the tooth, said generated rotation motion defining:
- a first motion vector in a first direction at a portion of a first side of the tooth; and
- a second motion vector, in a second direction opposing said first direction, at a portion of a second side of the tooth, the second side of the tooth opposing the first side of the tooth;
- wherein a first axis extending between said first of said plurality of lingual electrodes and said first of said plurality of buccal electrodes is parallel and aligned with said first motion vector,
- wherein a second axis extending between said second of said plurality of lingual electrodes and said second of said plurality of buccal electrodes is parallel and aligned with said second motion vector, and
- wherein the direction of said orthogonal current generated between said first of said plurality of lingual electrodes and said first of said plurality of buccal electrodes and the direction of said orthogonal current generated between said second of said plurality of lingual electrodes and said second of said plurality of buccal electrodes are arranged to expedite bone resorption and deposition caused responsive to said provided rotational orthodontic force.

26. The vestibular electronic orthodontic appliance expediter of claim 24, wherein the vestibular electronic orthodontic appliance expediter is shaped such as to be completely tissue borne.

27. The vestibular electronic orthodontic appliance expediter of claim 26, wherein each of said plurality of lingual electrodes and each of said plurality of buccal electrodes extends from 1 millimeter apical to the gingival margin to the mucogingival junction of the gum.

28. The vestibular electronic orthodontic appliance expediter of claim 26, wherein each of said plurality of lingual electrodes and each of said plurality of buccal electrodes extends from 1 millimeter apical to the gingival margin to at least one millimeter over the mucosal tissue of the gum.

29. The vestibular electronic orthodontic appliance expediter of claim 24, wherein said control circuitry is further arranged to generate a plurality of parallel currents via said plurality of lingual electrodes and said plurality of buccal electrodes,
- wherein each of said plurality of parallel current is generated between one of:
  - a respective one of said plurality of lingual electrodes and one of said plurality of lingual electrodes adjacent thereto; and
  - a respective one of said plurality of buccal electrodes and one of said plurality of buccal electrodes adjacent thereto.

30. A vestibular electronic orthodontic appliance expediter comprising:
- a lingual sub-member and a buccal sub-member, said lingual sub-member arranged to fit a lingual contour of a gum of a patient over a lingual side of an alveolar bone of the patient, said buccal sub-member arranged to fit a buccal contour of a gum of the patient over a buccal side of the alveolar bone;
- a control circuitry;
- a plurality of lingual electrodes disposed on said lingual sub-member, each of said plurality of lingual electrodes adapted to be juxtaposed with a respective one of a plurality of tooth sockets within the alveolar bone;
- a plurality of buccal electrodes disposed on said buccal sub-member, each of said plurality of buccal electrodes adapted to be juxtaposed with a respective one of the plurality of tooth sockets within the alveolar bone; and
- a plurality of adjustable pressure elements,
- wherein said control circuitry is arranged to generate, via said plurality of lingual electrodes and said plurality of buccal electrodes at least one of:
  - a plurality of orthogonal currents, each controlled separately responsive to said control circuitry; and
  - a plurality of parallel currents, each controlled separately responsive to said control circuitry,
- wherein each of said plurality of orthogonal currents is generated between a respective one of said plurality of lingual electrodes and a respective one of said plurality of buccal electrodes, said respective ones associated with the same respective tooth socket,
- wherein each of said plurality of parallel currents is generated between one of:
  - a respective one of said plurality of lingual electrodes and one of said plurality of lingual electrodes adjacent thereto; and
  - between a respective one of said plurality of buccal electrodes and one of said plurality of buccal electrodes adjacent thereto, and
- wherein each of said adjustable pressure elements is arranged to apply an adjustable amount of pressure to a respective one of said plurality of lingual electrodes and said plurality of buccal electrodes.

31. The vestibular electronic orthodontic appliance expediter of claim 30, wherein each of said adjustable pressure elements is arranged to expand responsive to air being injected therewithin, said adjustable amount of pressure applied responsive to said injected air.

32. The vestibular electronic orthodontic appliance expediter of claim 30, wherein each of said adjustable pressure elements is arranged to expand responsive to a pressure member being inserted therewithin, said adjustable amount of pressure applied responsive to said inserted pressure member.

* * * * *